(12) United States Patent
Maliga et al.

(10) Patent No.: US 7,285,700 B2
(45) Date of Patent: Oct. 23, 2007

(54) PLASTID DIRECTED DNA CONSTRUCTS COMPRISING CHIMERIC PLASTID TARGETING REGIONS, VECTORS CONTAINING SAME AND METHODS OF USE THEREOF

(75) Inventors: Pal Maliga, East Brunswick, NJ (US); Marina Skarjinskaia, Highland Park, NJ (US); Zora Svab Maliga, East Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 357 days.

(21) Appl. No.: 10/460,716

(22) Filed: Jun. 12, 2003

(65) Prior Publication Data

US 2003/0200568 A1    Oct. 23, 2003

Related U.S. Application Data

(63) Continuation of application No. 09/524,087, filed on Mar. 13, 2000, now abandoned, which is a continuation-in-part of application No. 09/142,114, filed as application No. PCT/US97/03444 on Mar. 6, 1997, now Pat. No. 6,376,744.

(60) Provisional application No. 60/012,916, filed on Mar. 6, 1996.

(51) Int. Cl.
```
C12N 15/82    (2006.01)
C12N 5/04     (2006.01)
C12N 5/10     (2006.01)
A01H 5/00     (2006.01)
C12N 15/29    (2006.01)
```
(52) U.S. Cl. .............. 800/278; 800/289; 800/300; 800/306; 800/317.3; 435/320.1; 435/419; 435/463; 536/23.6

(58) Field of Classification Search ............ 800/278, 800/306, 289, 300; 435/468, 419, 320.1
See application file for complete search history.

(56) References Cited

U.S. PATENT DOCUMENTS

| | | | |
|---|---|---|---|
| 5,451,513 A | | 9/1995 | Maliga et al. |
| 5,545,817 A | * | 8/1996 | McBride et al. ............ 800/287 |
| 5,545,818 A | | 8/1996 | McBride et al. |
| 5,576,198 A | | 11/1996 | McBride et al. |
| 5,877,402 A | | 3/1999 | Maliga et al. |
| 5,925,806 A | * | 7/1999 | McBride et al. ............ 800/298 |

FOREIGN PATENT DOCUMENTS

EP    0142924 A2    5/1985
EP    0589841 A2    3/1994

OTHER PUBLICATIONS

Chasan, R. Plant Cell 4(1): 1-2 (Jan. 1992).*
de Lanversin et al. Theoretical and Applied Genetics 76(3): 443-448 (1988).*
Bonnard et al. Current Genetics 9(5): 417-422 (1985).*
Maid et al. Plant Molecular Biology 16(4): 537-546 (1991).*
Massenet et al. Plant Molecular Biology 10(1): 53-63 (1987).*
Ishikura et al. Journal of Bioscience and Bioengineering 87(3): 307-314 (1999).*
Blowers et al. Plant Cell 2(11): 1059-1070 (Nov. 1990).*
Sikdar et al. Plant Cell Reports 18: 20-24 (1998).*
Kanevski et al. Plant Physiology 111(1): 133-141 (Jan. 1999).*
Bohnert et al. Molecular and General Genetics 179(3): 539-545 (1980); Abstract only.*
Keus et al. Nucleic Acids Research 11(18): 6465-6474 (1983).*
Jeffrey M. Staub, et al. Long Regions of Homologous DNA are Incorporated into the Tobacco Plastid Genome by Transformation. The Plant Cell. (Jan. 1992) 4:39-45.
Sumita Chaudhuri, et al. Site-Specific factor involved in the editing of the psbL mRNA in tobacco plastids: The EMBO Journal. (1995) 14(12):2951-2957.
Jeffrey M. Staub, et al. Expression of a chimeric uidA gene indicates that polycistronic mRNAs are efficiently translated in tobacco plastids. The Plant Journal. (1995) 7(5):845-848.
Jeffrey M. Staub, et al. Marker rescue from the Nicotiana tabacum plastid genome using a plastid/*Escherichia coli* shuttle vector. Mol. Gen. Genet. (1995) 249:37-42.
H. -U. Koop. 1995, Plastid Transformation by Polyethylene Glycol Treatment of Protoplasts and Regeneration of Transplastomic Tobacco Plants. In: Gene Transfer to Plants, pp. 75-82, Potrykus, ed. New York; Springer-Verlag.
Oleg V. Zoubenko, et al. Efficient targeting of foreign genes into the tobacco plastid genome. Nucleic Acids Research. (1994) 22(19):3819-3824.
Helaine Carrer, et al. Kanamycin resistance as a selectable marker for plastid transformation in tobacco. Mol. Gen Genet. (1993) . . . 241: 49-56.
Christina M. Richards, et al. Survey of plastid RNA abundance during tomato fruit ripening: the amounts of RNA from the ORF 2280 region increase in chromoplasts. Plant Molecular Biology. (1991) 17:1179-1188.

* cited by examiner

*Primary Examiner*—David T Fox
(74) *Attorney, Agent, or Firm*—Dann, Dorfman, Herrell & Skillman; Kathleen D. Rigaut

(57) ABSTRACT

This invention relates to methods and compositions for obtaining *Arabidopsis* and *Brassica* plants. Specifically, the method provides culturing protocols and compositions that facilitate the regeneration of transformed plants following delivery of beneficial DNA molecules.

34 Claims, 14 Drawing Sheets

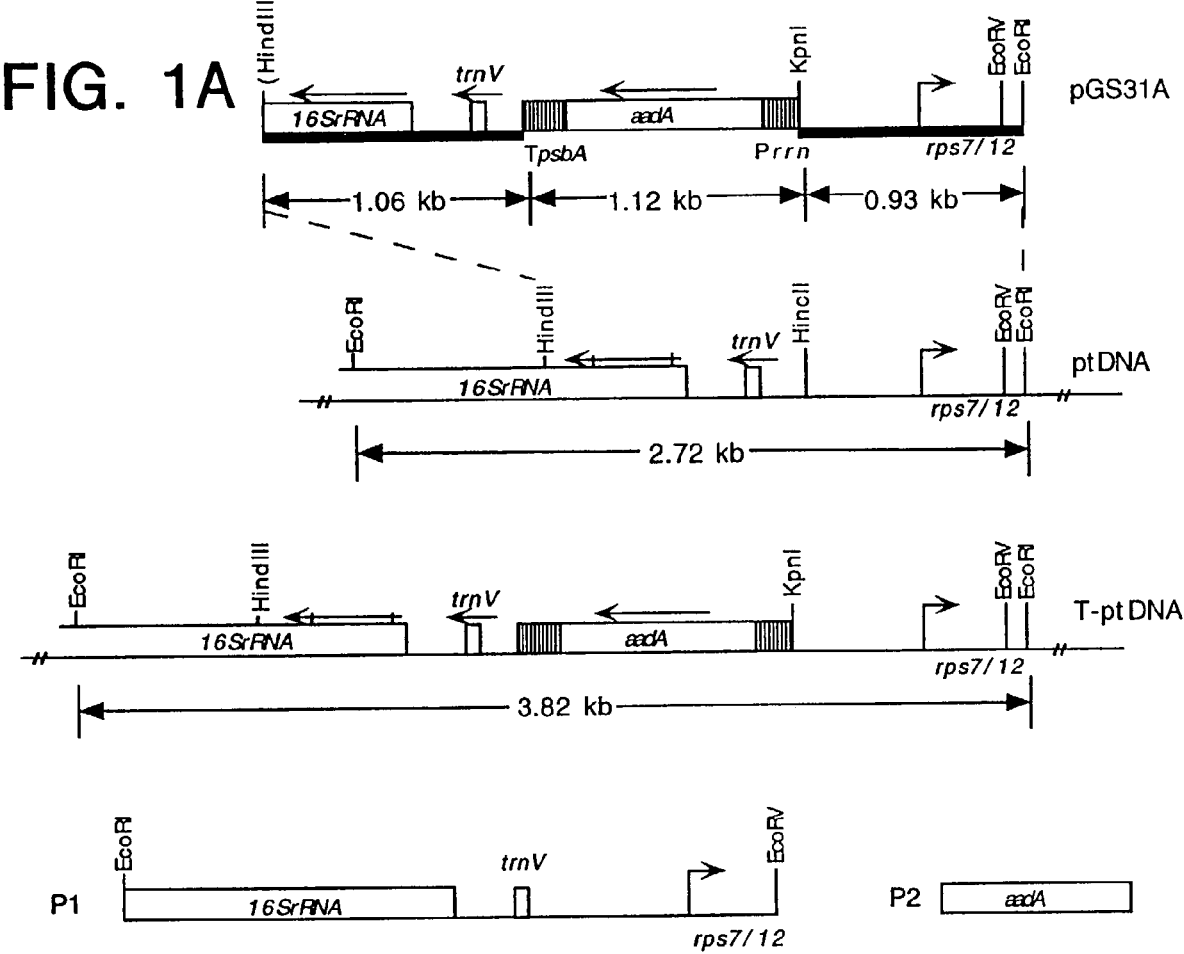
FIG. 1A
FIG. 1B
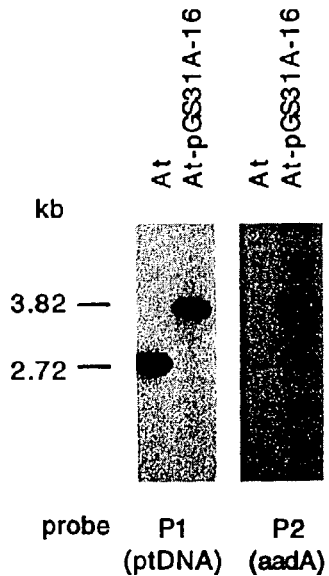
FIG. 1C

*Hind*III

```
   1  AAGCTTGGTA GTTTCCACCG CCTGTCCAGG GTTGAGCCCT GGGATTTGAC
  51  GGCGGACTTA AAAAGCCACC TACAGACGCT TTACGCCCAA TCATTCCGGA
 101  TAACGCTTGC ATCCTCTGTA TTACCGCGGC TGCTGGCACA GAGTTAGCCG
 151  ATGCTTATTC CCCAGATACC GTCATTGCTT CTTCTCTGGG AAAAGAAGTT
 201  CAGGACCCGT AGGCCTTCTA CCTCCACGCG GCATTGCTCC GTCAGGCTTT
 251  CGCCCATTGC GGAAAATTCC CCACTGCTGC CTCCCGTAGG AGTCTGGGCC
 301  GTGTCTCAGT CCCAGTGTGG CTGATCATCC TCTCGGACCA GCTACTGATC
 351  ATCGCCTTGG TAAGCTATTG CCTCACCAAC TAGCTAATCA GACGCGAGCC
 401  CCTCCTCGGG CGGATTCCTC CTTTTGCTCC TCAGCTACGG GGTATTAGCA
 451  GCCGTTTCCA GCTGTTGTTC CCCTCCCAAG GGNAGGTTCT TACGCGTTAC
 501  TCAcCNGTCC GCCACTGGAA ACACCACTTC CCGTCCGACT TGCATGTGTT
 551  AAGCATGCCG CCAGCGTTCA TCCTGAGCCA GGATCGAACT CTCCATGAGA
 601  TTCATAGTTG CATTACTTAT AGCTTCCTTC TTCGTAGACA AAGCTGATTC
 651  GGAATTGTCT TTCATTCCAA GTCATAACTT GTATCCATGC GCTTCATATT
 701  CGCATGGAGT TCGCTCCAG AAATATAGCT ACCCCTACCC CCTCACGTCA
 751  ATCCCACGAG CCTCTTATCC ATTCTTATTC GATCACAGCG AGGGAGCAAG
 801  TCAAAATAGA AAAACTCACA TTCATTGGGT TTAGGGATAA TCAGGCTCGA
 851  ACTGATGACT TCCACCACGT CAAGGTGACA CTCTACCGCT GAGTTATATC
 901  CCTTCCCCCA TCAAGAAATA GAACTGACTA ATCCTAAGTC AAAGGGTCGA
 951  GAAACTCAAG GCCACTATTC TTGAACAACT TGGATTGGAG CCGGGCTTTC
1001  CTTTCGCACT TTATACGGGT ATGAAATGAA AATAATGGAA AAAGTTGGAT
1051  TCAATTGTCA ACTACTCCTA TCGGAAATAG GATTGACTAC GGATTCGAGC
1101  CATAGCACAT GGTTTCATAA AACCGTACGA TTCTCCCGAT CTAAATCAAG
1151  CCGGTTTTAC ATGAAGAAGA TTTGACTCGG CATGTTCTAT TCGATACGGG
1201  TAGGAGAAAC GGTATTCTTT TCTTAAACTT CAAAAAATAG AGAAATAAGA
1251  ACCAAGTCAA GATGATACGG ATTAATCCTT TATTCTTGCG CCAAAGATCT
1301  TCCTATTCCA AGGAACTGGA GTTACATCTC TTTTCCATTT CCATTCAAGA
1351  GTTCTTATGT GTTTCCACgC CCCTTTAAGA cCCCGAAAAA TCGACAAATT
1401  CCCTTTTCTT AGGACCACAT GCGAGATAAC GAAAAAAAAA AAGAGAGAAT
1451  GGTAACCCCA CGATTAACTA TTTTATTTAT GAATTTCATA GTAATAGAAA
1501  TACATGTCCT ACCGAAACAG AATTTGTAAC TTGCTATCCT ATCATCTTGC
1551  CTAGCAGGCA AAGATTTCAC TCCGCGAAAA AGATGATTCA TTCGGATCAA
1601  CATGAAAGCC CAACTACATT GCCAGAATTT ATATATTGGA AAGAGGTTTA
1651  CCTCCTTGCT TCTATGGTAC AATCCTCTTC CCGCGGAGCC TCCTTTCTTC
1701  TCGGTCCGCA GAGACAAAAT GTAGGACTGG TGCCAACAGT TAATCACGGA
1751  AGAAAGGACT CACTGCGCCA AGATCACTAA CTAATCTAAT AGAATAGAAA
1801  ATCCTAATAT AATAGAAAAG AAAAGAACTG TCTTTTCTGA TACTTATGTA
1851  TACTTTCCCC GGTTCCGTTG CTACTGCGGS TTTACGCAAT TGATCGGATC
1901  ATCTAGATAT CCCTTCAACA CAACATAGGT CGTCGAAAGG ATCTCGGAGA
1951  CCCGCCAAAG CACGAAAGCC AGAATCTTTC AGAAAATGAA TTC
```

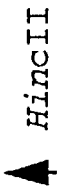

*Hinc*II

*Eco*RI

FIG. 5

```
   1  CATGAATAAA TGCAAGAAAA TAACCTCTCC TTCTTTTTCT ATAATGTAAA
  51  CAAAAAGTC  TATGTAAGTA AAATACTAGT AAATAAATAA AAAGAAAAAA
 101  AGAAAGGAGC AATAGCACCC TCTTGATAGA ACAAGAAAAT GATTATTGCT
 151  CCTTTCTTTT CAAAACCTCC TATAGACTAG GCCAGGATCg ctctagctag
 201  acattatttg ccgactacct tggtgatctc gcctttcacg tagtggacaa
 251  attcttccaa ctgatctgcg cgcgaggcca agcgatcttc ttcttgtcca
 301  agataagcct gtctagcttc aagtatgacg ggctgatact gggccggcag
 351  gcgctccatt gcccagtcgg cagcgacatc cttcggcgcg attttgccgg
 401  ttactgcgct gtaccaaatg cgggacaacg taagcactac atttcgctca
 451  tcgccagccc agtcgggcgg cgagttccat agcgttaagg tttcatttag
 501  cgcctcaaat agatcctgtt caagaaccgg atcaaagagt cctccgccg
 551  ctggacctac caaggcaacg ctatgttctc ttgcttttgt cagcaagata
 601  gccagatcaa tgtcgatcgt ggctggctcg aagatacctg caagaatgtc
 651  attgcgctgc cattctccaa attgcagttc gcgcttagct ggataacgcc
 701  acggaatgat gtcgtcgtgc acaacaatgg tgacttctac agcgcggaga
 751  atctcgctct ctccagggga agccgaagtt ccaaaaggt cgttgatcaa
 801  agctcgccgc gttgtttcat caagccttac ggtcaccgta accagcaaat
 851  caatatcact gtgtggcttc aggccgccat ccactgcgga gccgtacaaa
 901  tgtacggcca gcaacgtcgg ttcgagatgg cgctcgatga cgccaactac
 951  ctctgatagt tgagtcgata cttcggcgat caccgcttcT GCcatAAATC
1001  CCTCCCTACA ACTGTATCCA AGCGCTTCGT ATTCGCCCGG AGTTCGCTCC
1051  CAGAAATATA GCCATCCCTG CCCCCTCACG TCAATCCCAC GAGCCTCTTA
1101  TCCATTCTCA TTGAACGACG GCGGGGAGC  tttgggtacc gag
```

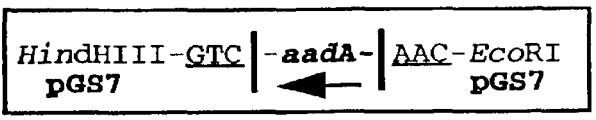

FIG. 6

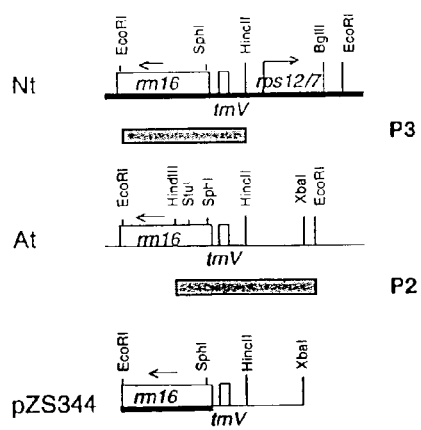
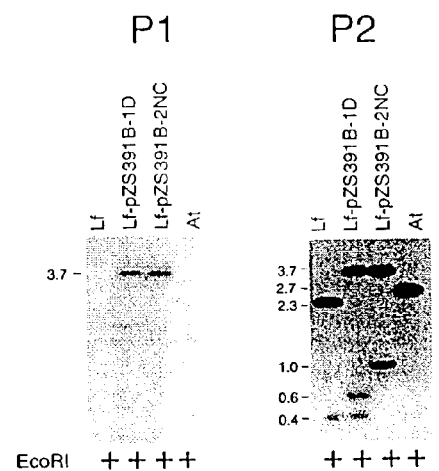
Fig. 8A
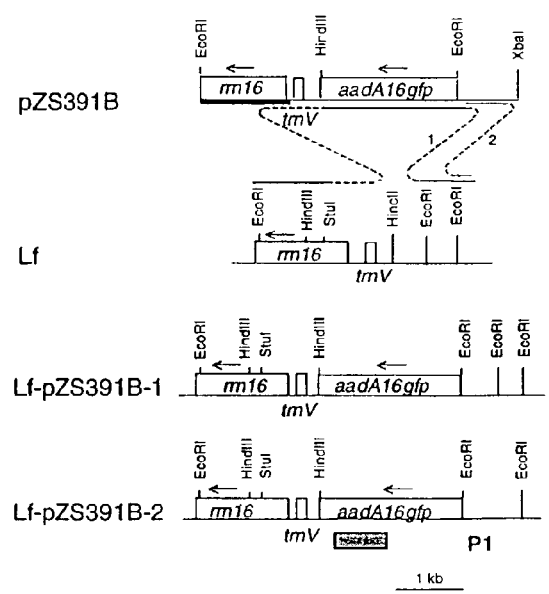
Fig. 8B
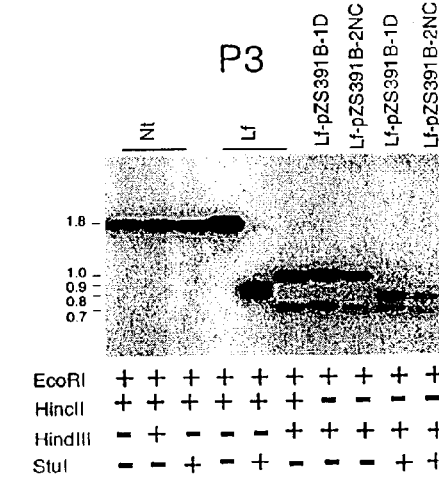
Fig. 8C

```
   1  AATTCACCGC CGTATGGCTG ACCGGCGATT ACTAGCGATT CCGGCTTCAT
  51  GCAGGCGAGT TGCAGCCTGC AATCCGAACT GAGGACGGGT TTTTGGGGTT
 101  AGCTCACCCT CGCGGGATCG CGACCCTTTG TCCCGGCCAT TGTAGCACGT
 151  GTGTCGCCCA GGGCATAAGG GGCATGATGA CTTGACGTCA TCCTCACCTT
 201  CCTCCGGCTT ATCACCGGCA GTCTGTTCAG GGTTCCAAAC TCAACGATGG
 251  CAACTAAACA CGAGGGTTGC GCTCGTTGCG GGACTTAACC CAACACCTTA
 301  CGGCACGAGC TGACGACAGC CATGCACCAC CTGTGTCCGC GTTCCCGAAG
 351  GCACCCCTCT CTTTCAAGAG GATTCGCGGC ATGTCAAGCC CTGGTAAGGT
 401  TCTTCGCTTT GCATCGAATT AAACCACATG CTCCACCGCT TGTGCGGGCC
 451  CCCGTCAATT CCTTTGAGTT TCATTCTTGC GAACGTACTC CCCAGGCGGG
 501  ATACTTAACG CGTTAGCTAC AGCACTGCAC GGGTCGATAC GCACAGCGCC
 551  TAGTATCCAT CGTTTACGGC TAGGACTACT GGGGTATCTA ATCCCATTCG
 601  CTCCCCTAGC TTTCGTCTCT CAGTGTCAGT GTCGGCCCAG CAGAGTGCTT
 651  TCGCCGTTGG TGTTCTTTCC GATCTCTACG CATTTCACCG CTCCACCGGA
 701  AATTCCCTCT GCCCCTACCG TACTCCAGCT TGGTAGTTTC CACCGCCTGT
 751  CCAGGGTTGA GCCCTGGGAT TTGACGGCGG ACTTAAAAAG CCACCTACAG
 801  ACGCTTTACG CCCAATCATT CCGGATAACG CTTGCATCCT CTGTATTACC
 851  GCGGCTGCTG GCACAGAGTT AGCCGATGCT TATTCCCCAG ATACCGTCAT
 901  TGCTTCTTCT CCGGGAAAAG AAGTTCACGA CCCGTGGGCC TTCTACCTCC
 951  ACGCGGCATT GCTCCGTCAG CTTTCGCCCA TTGCGGAAAA TTCCCCACTG
1001  CTGCCTCCCG TAGGAGTCTG GGCCGTGTCT CAGTCCCAGT GTGGCTGATC
1051  ATCCTCTCGG ACCAGCTACT GATCATCGCC TTGGTAAGCT ATTGCCTCAC
1101  CAACTAGCTA ATCAGACGCG AGCCCCTCCT CGGGCGGATT CCTCCTTTTG
1151  CTCCTCAGCC TACGGGGTAT TAGCAGCCGT TTCCAGCTGT TGTTCCCCTC
1201  CCAAGGGCAG GTTCTTACGC GTTACTCACC CGTCCGCCAC TGGAAACACC
1251  ACTTCCCGTC CGACTTGCAT GTGTTAAGCA TGCCGCCAGC GTTCATCCTG
1301  AGCCAGGATC GAACTCTCCA TGAGATTCAT AGTTGCATTA CTTATAGCTT
1351  CCTTCTTCGT AGACAAAGCT GATTCGGAAT TGTCTTTCAT TCCAAGTCAT
1401  AACTTGTATC CATGCGCTTC ATATTCGCAT GGAGTTCGCT CCCAGAAATA
1451  TAGCTACCCC TACCCCCTCA CGTCAATCCC ACGAGCCTCT TATCCATTCT
```

Fig. 11A

```
1501  TATTCGATCA CAGCGAGGGA GCAAGTCAAA ATAGAAAAAC TCACATTCAT
1551  TGGGTTTAGG GATAATCAGG CTCGAACTGA TGACTTCCAC CACGTCAAGG
1601  TGACACTCTA CCGCTGAGTT ATATCCCTTC CCCCATCAAG AAATAGAACT
1651  GACTAATCCT AAGTCAAAGG GTCGAGAAAC TCAAGGCCAC TATTCTTGAA
1701  CAACTTGGAT TGGAGCCGGG CTTTCCTTTC GCACTTTATA CGGGTATGAA
1751  ATGAAAATAA TGGAAAAGT TGGATTCAAT TGTCgacggt atcgataagc
1801  tttGATCCCC CATGAATAAA TGCAAGAAAA TAACCTCTCC TTCTTTTTCT
1851  ATAATGTAAA CAAAAAAGTC TATGTAAGTA AATACTAGT AAATAAATAA
1901  AAAGAAAAAA AGAAAGGAGC AATAGCACCC TCTTGATAGA ACAAGAAAAT
1951  GATTATTGCT CCTTTCTTTT CAAAACCTCC TATAGACTAG GCCAGGATCG
2001  CtctagagcC TTATTTGTAT AGTTCATCCA TGCCATGTGT AATCCCAGCA
2051  GCTGTTACAA ACTCAAGAAG GACCATGTGG TCTCTCTTTT CGTTGGGATC
2101  TTTCGAAAGG GCAGATTGTG TGGACAGGTA ATGGTTGTCT GGTAAAAGGA
2151  CAGGGCCATC GCCAATTGGA GTATTTTGTT GATAATGGTC TGCTAGTTGA
2201  ACGCTTCCAT CTTCAATGTT GTGTCTAATT TTGAAGTTAG CTTTGATTCC
2251  ATTCTTTTGT TTGTCTGCCG TGATGTATAC GTTGTGGGAG TTGTAGTTGT
2301  ATTCCAACTT GTGGCCGAGG ATGTTTCCGT CCTCCTTGAA ATCGATTCCC
2351  TTAAGCTCGA TCCTGTTGAC GAGGGTGTCT CCCTCAAACT TGACTTCAGC
2401  ACGTGTCTTG TAGTTCCCGT CGTCCTTGAA AGAGATGGTC CTCTCCTGCA
2451  CGTATCCCTC AGGCATGGCG CTCTTGAAGA AGTCGTGCCG CTTCATATGA
2501  TCTGGGTATC TTGAAAAGCA TTGAACACCA TAAGAGAAAG TAGTGACAAG
2551  TGTTGGCCAa GGAACAGGTA GTTTTCCAGT AGTGCAAATA AATTTAAGGG
2601  TAAGTTTTCC GTATGTTGCA TCACCTTCAC CCTCTCCACT GACAGAAAAT
2651  TTGTGCCCAT TAACATCACC ATCTAATTCA ACAAGAATTG GGACAACTCC
2701  AGTGAAAAGT TCTTCTCCTT TACTagcCAT ggcgacttta agaccttcta
2751  ctagctccaa ttttccttca acaagttcTT TGCCcACTAC CTTGGTGATC
2801  TCGCCTTTCA CGTAGTGGAC AAATTCTTCC AACTGATCTG CGCGCGAGGC
2851  CAAGCGATCT TCTTCTTGTC CAAGATAAGC CTGTCTAGCT TCAAGTATGA
2901  CGGGCTGATA CTGGGCCGGC AGGCGCTCCA TTGCCCAGTC GGCAGCGACA
2951  TCCTTCGGCG CGATTTTGCC GGTTACTGCG CTGTACCAAA TGCGGGACAA
```

Fig. 11B

```
3001  CGTAAGCACT ACATTTCGCT CATCGCCAGC CCAGTCGGGC GGCGAGTTCC

3051  ATAGCGTTAA GGTTTCATTT AGCGCCTCAA ATAGATCCTG TTCAGGAACC

3101  GGATCAAAGA GTTCCTCCGC CGCTGGACCT ACCAAGGCAA CGCTATGTTC

3151  TCTTGCTTTT GTCAGCAAGA TAGCCAGATC AATGTCGATC GTGGCTGGCT

3201  CGAAGATACC TGCAAGAATG TCATTGCGCT GCCATTCTCC AAATTGCAGT

3251  TCGCGCTTAG CTGGATAACG CCACGGAATG ATGTCGTCGT GCACAACAAT

3301  GGTGACTTCT ACAGCGCGGA GAATCTCGCT CTCTCCAGGG GAAGCCGAAG

3351  TTTCCAAAAG GTCGTTGATC AAAGCTCGCC GCGTTGTTTC ATCAAGCCTT

3401  ACGGTCACCG TAACCAGCAA ATCAATATCA CTGTGTGGCT TCAGGCCGCC

3451  ATCCACTGCG GAGCCGTACA AATGTACGGC CAGCAACGTC GGTTCGAGAT

3501  GGCGCTCGAT GACGCCAACT ACCTCTGATA GTTGAGTCGA TACTTCGGCG

3551  ATCACCGCTT CgctagcTGA CATAAATCCC TCCCTACAAC TCATGAATTA

3601  AGAATTtTCA CAACAACAAG GTCTACTCGA CTCCCAGAAA TATAGCCATC

3651  CCTGCCCCCT CACGTCAATC CCACGAGCCT CTTATCCATT CTCATTGAAC

3701  GACGGCGGGG GAGCgagctc gaattcctgc agcccAACTA CTCCTATCGG

3751  AAATAGGATT GACTACGGAT TCGAGCCATA GCACATGGTT TCATAAAACC

3801  GTACGATTCT CCCGATCTAA ATCAAGCCGG TTTTACATGA AGAAGATTTG

3851  ACTCGGCATG TTCTATTCGA TACGGGTAGG AGAAACGGTA TTCTTTTCTT

3901  AAACTTAAAA AAATAGAGAA ATAAGAACCA AGTCAAGATG ATACGGATTA

3951  ATCCTTTATT CTTGCGCCAA AGATCTTCCT ATTTCCAAAG GAACTGGAGT

4001  TACATCTCTT TTCCATTTCC ATTCAAGAGT TCTTATGTGT TTCCACGCCC

4051  CTTTAAGACC CCGAAAAATC GACAAATTCC CTTTTCTTAG GACCACATGC

4101  GAGATAACGA AAAAAAAAA GAGAGAATGG TAACCCCACG ATTAACTATT

4151  TTATTTATGA ATTTCATAGT AATAGAAATA CATGTCCTAC CGAAACAGAA

4201  TTTGTAACTT GCTATCCTAT CATCTTGCCT AGCAGGCAAA GATTTCACTC

4251  CGCGAAAAAG ATGATTCATT CGGATCAACA TGAAAGCCCA ACTACATTGC

4301  CAGAATTTAT ATATTGGAAA GAGGTTTACC TCCGTGCTTC TATGGTACAA

4351  TCCTCTTCCC GCGGAGCCTC CTTTCTTCTC GGTCCGCAGA GACAAAATGT

4401  AGGACTGGTG CCAACAGTTA ATCACGGAAG AAAGGACTCA CTGCGCCAAG

4451  ATCACTAACT AATCTAATAG AATAGAAAAT CCTAATATAA TAGAAAAGAA
```

Fig. 11C

```
4501  AAGAACTGTC TTTTCTGTAT ACTTATGTAT ACTTTCCCCG GTTCCGTTGC
4551  TACTGCGGGC TTTACGCAAT TGATCGGATC ATCTAG
```

Fig. 11D

SEQUENCE LISTING

```
<160> NUMBER OF SEQ ID NOS: 8

<210> SEQ ID NO 1
<211> LENGTH: 1993
<212> TYPE: DNA
<213> ORGANISM: Arabidopsis thaliana
<220> FEATURE:
<221> NAME/KEY: unsure
<222> LOCATION: (483)...(483)
<223> OTHER INFORMATION: n = a, c, g, or t
<220> FEATURE:
<221> NAME/KEY: unsure
<222> LOCATION: (506)...(506)
<223> OTHER INFORMATION: n = a, c, g, or t
<220> FEATURE:
<221> NAME/KEY: unsure
<222> LOCATION: (1880)...(1880)
<223> OTHER INFORMATION: n = a, c, g, or t

<400> SEQUENCE: 1
aagcttggta gtttccaccg cctgtccagg gttgagccct gggatttgac ggcggactta      60
aaaagccacc tacagacgct ttacgcccaa tcattccgga taacgcttgc atcctctgta     120
```

```
ttaccgcggc tgctggcaca gagttagccg atgcttattc cccagatacc gtcattgctt      180
cttctctggg aaaagaagtt caggacccgt aggccttcta cctccacgcg gcattgctcc      240
gtcaggcttt cgcccattgc ggaaaattcc ccactgctgc ctcccgtagg agtctgggcc      300
gtgtctcagt cccagtgtgg ctgatcatcc tctcggacca gctactgatc atcgccttgg      360
taagctattg cctcaccaac tagctaatca gacgcgagcc cctcctcggg cggattcctc      420
cttttgctcc tcagctacgg ggtattagca gccgtttcca gctgttgttc ccctcccaag      480
ggnaggttct tacgcgttac tcaccngtcc gccactggaa acaccacttc ccgtccgact      540
tgcatgtgtt aagcatgccg ccagcgttca tcctgagcca ggatcgaact ctccatgaga      600
ttcatagttg cattacttat agcttccttc ttcgtagaca aagctgattc ggaattgtct      660
ttcattccaa gtcataactt gtatccatgc gcttcatatt cgcatggagt tcgctcccag      720
aaatatagct accctaccc cctcacgtca atcccacgag cctcttatcc attcttattc       780
gatcacagcg agggagcaag tcaaaataga aaaactcaca ttcattgggt ttagggataa      840
tcaggctcga actgatgact tccaccacgt caaggtgaca ctctaccgct gagttatatc      900
ccttccccca tcaagaaata gaactgacta atcctaagtc aaagggtcga gaaactcaag      960
gccactattc ttgaacaact tggattggag ccgggctttc ctttcgcact ttatacgggt     1020
atgaaatgaa ataatggaa aaagttggat tcaattgtca actactccta tcggaaatag      1080
gattgactac ggattcgagc catagcacat ggtttcataa aaccgtacga ttctcccgat     1140
ctaaatcaag ccggttttac atgaagaaga tttgactcgg catgttctat tcgatacggg     1200
taggagaaac ggtattcttt tcttaaactt caaaaaatag agaataaga accaagtcaa      1260 gatgatacgg attaatcctt tattcttgcg ccaaagatct tcctattcca aggaactgga     1320
gttacatctc ttttccattt ccattcaaga gttcttatgt gtttccacgc ccctttaaga     1380
ccccgaaaaa tcgacaaatt ccctttctt aggaccacat gcgagataac gaaaaaaaa      1440 aagagagaat ggtaacccca cgattaacta ttttatttat gaatttcata gtaatagaaa     1500
tacatgtcct accgaaacag aatttgtaac ttgctatcct atcatcttgc ctagcaggca     1560
aagatttcac tccgcgaaaa agatgattca ttcggatcaa catgaaagcc caactacatt     1620
gccagaattt atatattgga aagaggttta cctccttgct tctatggtac aatcctcttc     1680
ccgcggagcc tcctttcttc tcggtccgca gagacaaaat gtaggactgg tgccaacagt     1740
taatcacgga agaaaggact cactgcgcca agatcactaa ctaatctaat agaatagaaa     1800
atcctaatat aatagaaaag aaaagaactg tcttttctga tacttatgta tactttcccc     1860
ggttccgttg ctactgcggn tttacgcaat tgatcggatc atctagatat cccttcaaca     1920
caacataggt cgtcgaaagg atctcggaga cccgccaaag cacgaaagcc agaatctttc     1980
agaaaatgaa ttc                                                         1993

<210> SEQ ID NO 2
<211> LENGTH: 1143
<212> TYPE: DNA
<213> ORGANISM: Nicotinium tobacum

<400> SEQUENCE: 2
catgaataaa tgcaagaaaa taacctctcc ttctttttct ataatgtaaa caaaaaagtc       60
tatgtaagta aaatactagt aaataaataa aaagaaaaaa agaaggagc aatagcaccc      120 tcttgataga acaagaaaat gattattgct cctttctttt caaaacctcc tatagactag      180
```

-continued

| | |
|---|---|
| gccaggatcg ctctagctag acattatttg ccgactacct tggtgatctc gcctttcacg | 240 |
| tagtggacaa attcttccaa ctgatctgcg cgcgaggcca agcgatcttc ttcttgtcca | 300 |
| agataagcct gtctagcttc aagtatgacg ggctgatact gggccggcag gcgctccatt | 360 |
| gcccagtcgg cagcgacatc cttcggcgcg attttgccgg ttactgcgct gtaccaaatg | 420 |
| cgggacaacg taagcactac atttcgctca tcgccagccc agtcgggcgg cgagttccat | 480 |
| agcgttaagg tttcatttag cgcctcaaat agatcctgtt caagaaccgg atcaaagagt | 540 |
| tcctccgccg ctggacctac caaggcaacg ctatgttctc ttgcttttgt cagcaagata | 600 |
| gccagatcaa tgtcgatcgt ggctggctcg aagatacctg caagaatgtc attgcgctgc | 660 |
| cattctccaa attgcagttc gcgcttagct ggataacgcc acggaatgat gtcgtcgtgc | 720 |
| acaacaatgg tgacttctac agcgcggaga atctcgctct ctccagggga agccgaagtt | 780 |
| tccaaaaggt cgttgatcaa agctcgccgc gttgtttcat caagccttac ggtcaccgta | 840 |
| accagcaaat caatatcact gtgtggcttc aggccgccat ccactgcgga gccgtacaaa | 900 |
| tgtacggcca gcaacgtcgg ttcgagatgg cgctcgatga cgccaactac ctctgatagt | 960 |
| tgagtcgata cttcggcgac caccgcttct gccataaatc cctccctaca actgtatcca | 1020 |
| agcgcttcgt attcgcccgg agttcgctcc cagaaatata gccatccctg cccctcacg | 1080 |
| tcaatcccac gagcctctta tccattctca ttgaacgacg gcggggagc tttgggtacc | 1140 |
| gag | 1143 |

<210> SEQ ID NO 3
<211> LENGTH: 1417
<212> TYPE: DNA
<213> ORGANISM: Artificial Sequence
<220> FEATURE:
<223> OTHER INFORMATION: Synthetic construct

<400> SEQUENCE: 3

| | |
|---|---|
| gaattcgagc tcggtaccca agctcccccc gccgtcgttc aatgagaatg gataagaggc | 60 |
| tcgtgggatt gacgtgaggg ggcagggatg gctatatttc tgggagcgaa ctccgggcga | 120 |
| atacgaagcg cttggataca gttgtaggga gggatttatg tcaccacaaa cagaggggat | 180 |
| tgaacaagat ggattgcacg caggttctcc ggccgcttgg gtggagaggc tattcggcta | 240 |
| tgactgggca caacagacaa tcggctgctc tgatgccgcc gtgttccggc tgtcagcgca | 300 |
| ggggcgcccg gttcttttttg tcaagaccga cctgtccggt gccctgaatg aactccagga | 360 |
| cgaggcagcg cggctatcgt ggctggccac gacgggcgtt ccttgcgcag ctgtgctcga | 420 |
| cgttgtcact gaagcgggaa gggactggct gctattgggc gaagtgccgg ggcaggatct | 480 |
| cctgtcatct caccttgctc ctgccgagaa agtatccatc atggctgatg caatgcggcg | 540 |
| gctgcatacg cttgatccgg ctacctgccc attcgaccac caagcgaaac atcgcatcga | 600 |
| gcgagcacgt actcggatgg aagccggtct tgtcgatcag gatgatctgg acgaagagca | 660 |
| tcagggctc gcgccagccg aactgttcgc caggctcaag gcgcgcatgc ccgacggcga | 720 |
| ggatctcgtc gtgacacatg gcgatgcctg cttgccgaat atcatggtgg aaaatggccg | 780 |
| cttttctgga ttcatcgact gtggccggct gggtgtggcg gaccgctatc aggacatagc | 840 |
| gttggctacc cgtgatattg ctgaagagct tggcggcgaa tgggctgacc gcttcctcgt | 900 |
| gctttacggt atcgccgctc ccgattcgca gcgcatcgcc ttctatcgcc ttcttgacga | 960 |
| gttcttctga gcgggactct ggggttcgga tcgatcctct agagcgatcc tggcctagtc | 1020 |
| tataggaggt tttgaaaaga aaggagcaat aatcattttc ttgttctatc aagagggtgc | 1080 |

| | |
|---|---|
| tattgctcct ttctttttt cttttattt atttactagt attttactta catagacttt | 1140 |
| tttgtttaca ttatagaaaa agaaggagag gttattttct tgcatttatt catgattgag | 1200 |
| tattctattt tgattttgta tttgtttaaa ttgtgaaata gaacttgttt ctcttcttgc | 1260 |
| taatgttact atatctttt gatttttttt ttccaaaaaa aaaatcaaat tttgacttct | 1320 |
| tcttatctct tatctttgaa tatctcttat ctttgaaata ataatatcat tgaaataaga | 1380 |
| aagaagagct atattcgacc tgcaggcatg caagctt | 1417 |

<210> SEQ ID NO 4
<211> LENGTH: 4586
<212> TYPE: DNA
<213> ORGANISM: Artificial Sequence
<220> FEATURE:
<223> OTHER INFORMATION: Synthetic Construct

<400> SEQUENCE: 4

| | |
|---|---|
| aattcaccgc cgtatggctg accggcgatt actagcgatt ccggcttcat gcaggcgagt | 60 |
| tgcagcctgc aatccgaact gaggacgggt ttttggggtt agctcaccct cgcgggatcg | 120 |
| cgacccttg tcccggccat tgtagcacgt gtgtcgccca gggcataagg ggcatgatga | 180 |
| cttgacgtca tcctcacctt cctccggctt atcaccggca gtctgttcag ggttccaaac | 240 |
| tcaacgatgg caactaaaca cgagggttgc gctcgttgcg ggacttaacc caacacctta | 300 |
| cggcacgagc tgacgacagc catgcaccac ctgtgtccgc gttcccgaag gcacccctct | 360 |
| cttttcaagag gattcgcggc atgtcaagcc ctggtaaggt tcttcgcttt gcatcgaatt | 420 |
| aaaccacatg ctccaccgct tgtgcgggcc cccgtcaatt cctttgagtt tcattcttgc | 480 |
| gaacgtactc cccaggcggg atacttaacg cgttagctac agcactgcac gggtcgatac | 540 |
| gcacagcgcc tagtatccat cgtttacggc taggactact ggggtatcta atcccattcg | 600 |
| ctcccctagc tttcgtctct cagtgtcagt gtcggcccag cagagtgctt tcgccgttgg | 660 |
| tgttctttcc gatctctacg catttcaccg ctccaccgga aattccctct gccctaccg | 720 |
| tactccagct tggtagtttc caccgcctgt ccagggttga gccctgggat ttgacgcgg | 780 |
| acttaaaaag ccacctacag acgctttacg cccaatcatt ccggataacg cttgcatcct | 840 |
| ctgtattacc gcggctgctg gcacagagtt agccgatgct tattcccag ataccgtcat | 900 |
| tgcttcttct ccgggaaaag aagttcacga cccgtgggcc ttctacctcc acgcggcatt | 960 |
| gctccgtcag ctttcgccca ttgcggaaaa ttccccactg ctgcctcccg taggagtctg | 1020 |
| ggccgtgtct cagtcccagt gtggctgatc atcctctcgg accagctact gatcatcgcc | 1080 |
| ttggtaagct attgcctcac caactagcta atcagacgcg agccctcct cgggcggatt | 1140 |
| cctccttttg ctcctcagcc tacggggtat tagcagccgt ttccagctgt tgttcccctc | 1200 |
| ccaagggcag gttcttacgc gttactcacc cgtccgccac tggaaacacc acttcccgtc | 1260 |
| cgacttgcat gtgttaagca tgccgccagc gttcatcctg agccaggatc gaactctcca | 1320 |
| tgagattcat agttgcatta cttatagctt ccttcttcgt agacaaagct gattcggaat | 1380 |
| tgtctttcat tccaagtcat aacttgtatc catgcgcttc atattcgcat ggagttcgct | 1440 |
| cccagaaaata tagctacccc taccccctca cgtcaatccc acgagcctct tatccattct | 1500 |
| tattcgatca cagcgaggga gcaagtcaaa atagaaaaac tcacattcat tgggtttagg | 1560 |
| gataatcagg ctcgaactga tgacttccac cacgtcaagg tgacactcta ccgctgagtt | 1620 |
| atatcccttc ccccatcaag aaatagaact gactaatcct aagtcaaagg gtcgagaaac | 1680 |

-continued

```
tcaaggccac tattcttgaa caacttggat tggagccggg ctttcctttc gcactttata    1740
cgggtatgaa atgaaaataa tggaaaaagt tggattcaat tgtcgacggt atcgataagc    1800
tttgatcccc catgaataaa tgcaagaaaa taacctctcc ttcttttct ataatgtaaa     1860 caaaaagtc tatgtaagta aaatactagt aaataaataa aaagaaaaaa agaaaggagc     1920
aatagcaccc tcttgataga acaagaaaat gattattgct cctttctttt caaaacctcc    1980
tatagactag gccaggatcg ctctagagcc ttatttgtat agttcatcca tgccatgtgt    2040
aatcccagca gctgttacaa actcaagaag gaccatgtgg tctctctttt cgttgggatc    2100
tttcgaaagg gcagattgtg tggacaggta atggttgtct ggtaaaagga cagggccatc    2160
gccaattgga gtattttgtt gataatggtc tgctagttga acgcttccat cttcaatgtt    2220
gtgtctaatt ttgaagttag ctttgattcc attcttttgt ttgtctgccg tgatgtatac    2280
gttgtgggag ttgtagttgt attccaactt gtggccgagg atgtttccgt cctccttgaa    2340
atcgattccc ttaagctcga tcctgttgac gagggtgtct ccctcaaact tgacttcagc    2400
acgtgtcttg tagttcccgt cgtccttgaa agagatggtc ctctcctgca cgtatccctc    2460
aggcatggcg ctcttgaaga agtcgtgccg cttcatatga tctgggtatc ttgaaaagca    2520
ttgaacacca taagagaaag tagtgacaag tgttggccaa ggaacaggta gttttccagt    2580
agtgcaaata aatttaaggg taagttttcc gtatgttgca tcaccttcac cctctccact    2640
gacagaaaat ttgtgcccat taacatcacc atctaattca acaagaattg ggacaactcc    2700
agtgaaaagt tcttctcctt tactagccat ggcgacttta agaccttcta ctagctccaa    2760
ttttccttca acaagttctt tgcccactac cttggtgatc tcgcctttca cgtagtggac    2820
aaattcttcc aactgatctg cgcgcgaggc caagcgatct tcttcttgtc caagataagc    2880
ctgtctagct tcaagtatga cgggctgata ctgggccggc aggcgctcca ttgcccagtc    2940
ggcagcgaca tccttcggcg cgattttgcc ggttactgcg ctgtaccaaa tgcgggacaa    3000
cgtaagcact acatttcgct catcgccagc ccagtcgggc ggcgagttcc atagcgttaa    3060
ggtttcattt agcgcctcaa atagatcctg ttcaggaacc ggatcaaaga gttcctccgc    3120
cgctggacct accaaggcaa cgctatgttc tcttgctttt gtcagcaaga tagccagatc    3180
aatgtcgatc gtggctggct cgaagatacc tgcaagaatg tcattgcgct gccattctcc    3240
aaattgcagt tcgcgcttag ctggataacg ccacggaatg atgtcgtcgt gcacaacaat    3300
ggtgacttct acagcgcgga gaatctcgct ctctccaggg gaagccgaag tttccaaaag    3360
gtcgttgatc aaagctcgcc gcgttgtttc atcaagcctt acggtcaccg taaccagcaa    3420
atcaatatca ctgtgtggct tcaggccgcc atccactgcg gagccgtaca aatgtacggc    3480
cagcaacgtc ggttcgagat ggcgctcgat gacgccaact acctctgata gttgagtcga    3540
tacttcggcg atcaccgctt cgctagctga cataaatccc tccctacaac tcatgaatta    3600
agaattttca caacaacaag gtctactcga ctcccagaaa tatagccatc cctgcccct    3660 cacgtcaatc ccacgagcct cttatccatt ctcattgaac gacggcgggg gagcgagctc    3720
gaattcctgc agcccaacta ctcctatcgg aaataggatt gactacggat tcgagccata    3780
gcacatggtt tcataaaacc gtacgattct cccgatctaa atcaagccgg ttttacatga    3840
agaagatttg actcggcatg ttctattcga tacgggtagg agaaacggta ttcttttctt    3900
aaacttaaaa aaatagagaa ataagaacca agtcaagatg atacggatta atcctttatt    3960
cttgcgccaa agatcttcct atttccaaag gaactggagt tacatctctt ttccatttcc    4020
attcaagagt tcttatgtgt ttccacgccc ctttaagacc ccgaaaaatc gacaaattcc    4080
```

```
ctttctcttag gaccacatgc gagataacga aaaaaaaaaa gagagaatgg taaccccacg    4140
attaactatt ttatttatga atttcatagt aatagaaata catgtcctac cgaaacagaa    4200
tttgtaactt gctatcctat catcttgcct agcaggcaaa gatttcactc cgcgaaaaag    4260
atgattcatt cggatcaaca tgaaagccca actacattgc cagaatttat atattggaaa    4320
gaggtttacc tccgtgcttc tatggtacaa tcctcttccc gcggagcctc ctttcttctc    4380
ggtccgcaga gacaaaatgt aggactggtg ccaacagtta atcacggaag aaaggactca    4440
ctgcgccaag atcactaact aatctaatag aatagaaaat cctaatataa tagaaaagaa    4500
aagaactgtc ttttctgtat acttatgtat actttccccg gttccgttgc tactgcgggc    4560
tttacgcaat tgatcggatc atctag                                        4586

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
gcttgatgaa acaacgcgg                                                    19

<210> SEQ ID NO 6
<211> LENGTH: 25
<212> TYPE: DNA
<213> ORGANISM: Artificial Sequence
<220> FEATURE:
<223> OTHER INFORMATION: PCR Primer

<400> SEQUENCE: 6
ccaagcgatc ttcttcttgt ccaag                                             25

<210> SEQ ID NO 7
<211> LENGTH: 18
<212> TYPE: DNA
<213> ORGANISM: Artificial Sequence
<220> FEATURE:
<223> OTHER INFORMATION: PCR Primer

<400> SEQUENCE: 7
ccgacctgtc cggtgccc                                                     18

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
cacgacgaga tcctcgccg                                                    19
```

PLASTID DIRECTED DNA CONSTRUCTS COMPRISING CHIMERIC PLASTID TARGETING REGIONS, VECTORS CONTAINING SAME AND METHODS OF USE THEREOF

This application is a continuation of U.S. application Ser. No. 09/524,087, filed Mar. 13, 2000, now abandoned, which is a continuation-in-part of application Ser. No. 09/142,114, filed Feb. 5, 1999, now U.S. Pat. No. 6,376,744, which is a §371 of PCT/US97/03444 filed Mar. 6, 1997, which claims priority to provisional application No. 60/012,916, filed Mar. 6, 1996.

Pursuant to 35 U.S.C. Section 202(c), it is acknowledged that the United States government has certain rights in the invention describe herein, which was made in part with funds from the National Science Foundation Grant Number, MCB 93-05037.

FIELD OF THE INVENTION

The present invention relates to the field of transgenic plants. Specifically, the invention provides compositions and methods for the transformation of plastids in plants from the Cruciferae family.

BACKGROUND OF THE INVENTION

Several publications are parenthetically referenced in this application in order to more fully describe the state of the art to which this invention pertains. Full citations for these references are found at the end of the specification. The disclosure of each of these publications is incorporated by reference in the present specification as though set forth herein in full.

The plastid genome of higher plants is a circular double-stranded DNA molecule of 120-160 kb which may be present in 1,900-50,000 copies per leaf cell (Palmer, 1991; Bendich, 1987). Stable transformation of the tobacco plastid genome (plastome) has been achieved through the following steps: (i) introduction of transforming DNA, encoding antibiotic resistance, by the biolistic process (Svab et al. 1990a; Svab and Maliga 1993) or PEG treatment (Golds et al. 1993; O'Neill et al., 1993), (ii) integration of the transforming DNA by two homologous recombination events and (iii) selective elimination of the wild-type genome copies during repeated cell divisions on a selective medium. Spectinomycin resistance has been used as a selective marker encoded either in mutant plastid 16S ribosomal RNA genes Svab et al. 1990a; Staub and Maliga 1992; Golds et al. 1993), or conferred by the expression of an engineered bacterial aadA gene (Svab and Maliga 1993). Vectors which utilize aadA as a selectable marker gene and target the insertion of chimeric genes into the repeated region of tobacco plastid genome are available (Zoubenko et al., 1994). Selection of plastid transformants by kanamycin resistance, based on the expression of neomycin phosphotransferase (kan gene), is more difficult but also feasible (Carrer et al. 1993; Carrer and Maliga, 1995).

Transplastomic plants from agriculturally and pharmaceutically important species other than tobacco, are highly desirable. Expression of foreign genes of interest in the plastids of higher plants in the family Cruciferae provides several advantages over nuclear expression of foreign genes. These are 1) expression of exogenous DNA sequences in plastids eliminates the possibility of pollen transmission of transforming DNA; 2) high levels of protein expression are attainable; 3) the simultaneous expression of multiple genes as a polycistronic unit is feasible and 4) positional effects and gene silencing which may result following nuclear transformation are also eliminated.

SUMMARY OF THE INVENTION

The present invention provides improved methods for the generation of stably transformed, transplastomic plants. In one embodiment of the invention, cotyledon cells are cultured in high auxin liquid medium for a sufficient time period to stimulate uniform cell division. Initial culture is at a high density (50-200 cotyledons/20 ml). The cotyledons are then transferred to agar-solidified medium for delivery of exogenous, transforming DNA. Following delivery of transforming DNA, the cotyledons are transferred at a lower density (25-30/50 ml) to a medium containing high cytokinin levels and the selection agent to facilitate selection of transformants and plant regeneration. Presence of the exogenous DNA in the plastid genome is then confirmed by Southern blot analysis or PCR.

The transforming DNA molecules of the invention have several distinct features. These are 1) targeting segments flanking the foreign gene of interest may consist of plastid DNA sequences from the plant to be transformed, thereby facilitating homologous recombination of the transforming DNA into a predetermined region of the plastid genome or they may be chimeric in that they are derived from different species but possess partial homology that is sufficient to target insertion of transforming nucleic acid; 2) a selectable marker gene disposed within the targeting segment, conferring resistance to a selection agent; 3) 5' and 3' regulatory sequences derived from plastid DNA operably linked to sequences encoding a foreign gene of interest thereby enhancing expression of the transforming DNA and stability of encoded mRNA; and 4) at least one cloning site adjacent to the selectable marker gene for insertion of the foreign gene of interest which by itself is not selectable. Since the selectable marker gene and the foreign gene of interest form a heterologous block of contiguous sequence, integration of both genes into the plasid genome is effected.

In another embodiment of the invention, leaf cells are initially treated with high auxin media, followed by transformation with the transforming DNA and culturing in the presence of high cytokinin levels and a predetermined selection agent. Cells containing transformed plastids are maintained in the presence of the selection agent facilitating the obtention of homoplasmic cells which can then be regenerated into transplastomic plants.

In a further embodiment of the invention, tissue segments are directly placed on selective regeneration medium following bombardment.

In yet a further embodiment of the invention, an improved vector is provided which facilitates the generation of transplastomic plants. The improved vector comprises a targeting segment having first and second targeting sequences for facilitating recombination within the plastid genome, each of said first and second targeting sequences flanking at least one transgene of interest, at least one of said first and second targeting sequence being chimeric, said chimeric targeting sequence(s) having a first portion derived from the plant species targeted for transformation, and a second portion derived from a different plant species. Either the first, second or both targeting segments may be chimeric. In one embodiment the transgene comprises a selectable marker gene. In a preferred embodiment, the transgene comprises a polycistronic expression unit encoding both a selectable marker gene and a foreign gene of interest. Foreign genes of interest include without limitation, herbicide resistance genes, Bt genes, drought resistance genes, and other agriculturally and pharmaceutically beneficial protein encoding genes. Suitable selectable marker genes, include but are not limited to, those which confer resistance to kanamycin, streptomycin, and spectinomycin.

In yet another embodiment, transformed plant cells comprising the improved vectors of the invention are provided. Transformed plant cells include without limitation, cotyledon cells, leaf cells, hypocotyls and root cells. Transgenic plants comprising the improved vectors of the invention are also within the scope of the present claims.

Thus, the present invention provides novel methods and compositions for creating transplastomic plants. The genus *Arabidopsis* belongs to the mustard or crucifer family (Brassicaceae or Cruciferae), a widely distributed family of approximately 340 genera and 3350 species. The family is of significant economic importance as a source of vegetable crops, oil seeds, spices and, to a lesser extent, ornamentals. Much of its agricultural importance derives from the genus *Brassica*. Examples for *Brassica* ssp. of economic importance are: *Brassica napus* (oil seed), *Brassica juncea* (oil seed), *Brassica campestris* (oil seed), *Brassica oleracea* (broccoli, cauliflower, cabbage) *Brassica nigra* (black mustard) and *Brassica hirta* (white mustard).

Plastid transformation in *Arabidopsis thaliana* a model species for plant research (Meyerowitz and Sommerville, 1994) and *Brassica* ssp., an important agricultural crop is exemplified herein. These vectors and methods are suitable for transformation of plastids in other plants from the Cruciferae family.

BRIEF DESCRIPTION OF THE DRAWINGS

FIG. 1 is a schematic drawing illustrating the integration of aadA into the *Arabidopsis* plastid genome (ptDNA) after transformation with plasmid pGS31A. FIG. 1A shows a map of the transformation vector pGS31A, the ptDNA region containing the integrated spectinomcycin resistance (aadA) gene (T-ptDNA) and the cognate region of the wild-type ptDNA. 16SrDNA, rps12/7 and trnV are plastid genes (Shinozaki et al., 1986). FIG. 1B shows the regions of ptDNA contained in the Pi and P2 probes. FIG. 1C is an autoradiogram showing the results of Southern blot hybridization confirming integration of aadA in the plastid genome. The P1 targeting sequences hybridize to a 2.72-kb fragment in the wild-type (At) plants and to a larger, 3.82-k)b fragment in the transplastomic line (At-pGS31A-16). Note absence of wild-type fragment in transplastomic line. The aadA probe, P2, hybridizes only to the larger transplastomic fragment.

FIG. 5 is a sequence of the targeting region (SEQ ID NO: 1) of plasmid pGS7. The genes conferring resistance to kanamycin or spectinomycin will be inserted into the marked Hinc II site.

FIG. 6 is a sequence of the plastid targeting region (SEQ ID NO: 2) of plasmid pGS31A.

FIG. 8 is a schematic diagram showing the integration of foreign DNA into the *Lesquerella fendleri* plastid genome. FIG. 8A, Maps of cognate regions in the tobacco (Nt wt) and *Arabidopsis* (At wt) plastid genomes, and the plastid targeting region of vector pZS344. FIG. 8B, Integration of aadA16gfp into the *Lesquerella* plastid genome. Maps are shown for the plastid targeting region of vector pZS391B, the cognate region in the wild-type *Lesquerella* plastid genome (Lf wt) and transplastomic clones Lf-pZS391B-1 and Lf-pZS391B-2. FIG. 8C, DNA gel blots to test integration of vector sequences in the transplastomic clones. Blots were probed for: P1, aadA (NcoI-XbaI fragment; FIG. 8B); P2, HindIII-EcoRI targeting region fragment (FIG. 8A); P3, EcoRI-HincII targeting region fragment (FIG. 8A). Abbeviations: rrn16, 16S rRNA gene (Shinozaki et al. 1986).

FIG. 9 depicts transplastomic *Lesquerella fendleri*.

FIG. 10 shows the localization of the spectinomycin resistance mutation to the plastid rrn16 gene by loss of an AatII restriction site.

FIGS. 11A-D shows the nucleic acid sequence of the plastid targeting region (SEQ ID NO: 4) of pZS391b.

DETAILED DESCRIPTION OF THE INVENTION

Figure 2:
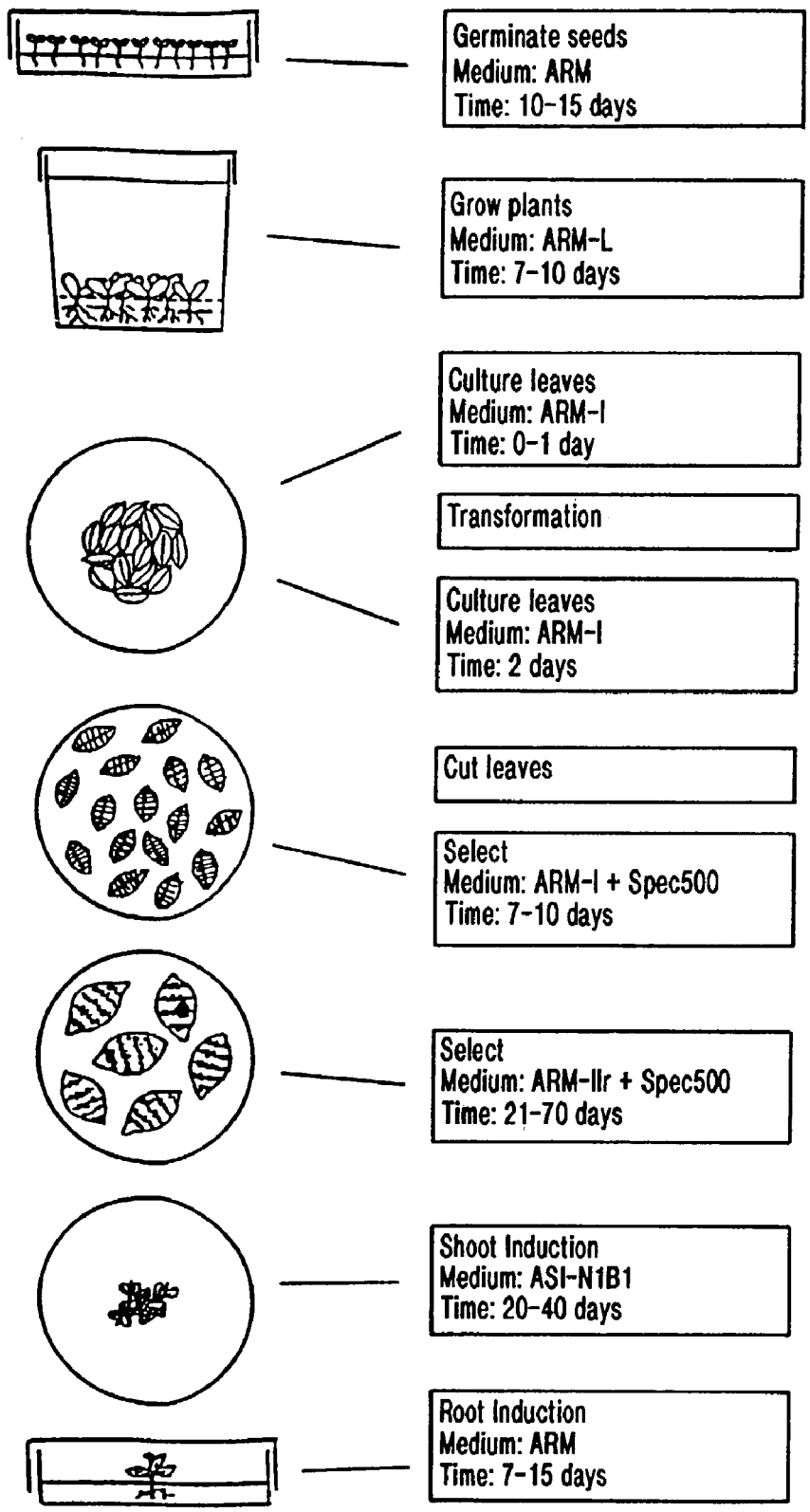
FIG. 2 is a schematic diagram of the plastid transformation protocol used for *Arabidopsis* leaves.

A protocol for the transformation of plastids in *Arabidopsis thaliana* and *Brassica napus* has now been developed and the methods utilized to create these transformants are set forth below. The use of *Arabidopsis* and *Brassica* in the following examples is meant to be illustrative of the methods of the invention. The methods disclosed herein may be adapted to other plants in the Cruciferae family.

The plastids of *Arabidopsis thaliana* have been transformed following biolistic delivery of transforming DNA into leaf cells on the surface of microscopic (1 µM) tungsten particles as described below in Example I. The transforming plasmid pGS31A, used for these experiments carries a spectinomycin resistance (aadA) gene flanked by plastid DNA sequences to target its insertion between trnV and the rps 12/7 operon. Integration of aadA by two homologous recombination events via the flanking ptDNA sequences and selective amplification of the transplastomes on spectinomycin medium yielded spectinomycin resistant cell lines. Regenerated plants were homoplasmic in that the plastid genome copies had been uniformly altered by the transforming DNA. The efficiency of plastid transformation was low, two in 201 bombarded leaf samples. However, none of the 98 plants regenerated from the two lines were fertile.

These fertility problems were likely attributable to extended periods of treatment with 2,4-D, an auxin (Van der Graaff and Hooykas, 1996). It is possible that shortening exposure time to this agent may overcome the fertility problem. The relatively long growth period of *Arabidopsis thaliana* to provide a suitable source of leaves for transformation also makes leaves a less desirable tissue source.

Cotyledons and leaves each contain an abundant number of plastid genome copies per cell. Additionally, cotyledons provide a more available tissue source. Accordingly, cotyledon cells have been utilized as recipients for transforming DNA as set forth in Example II below. Cotyledon cells are preferred over leaf cells for practicing the methods of the present invention due to the relatively short (7 days) culturing period to prepare the cells for bombardment with transforming DNA. Another advantage to using cotyledon cells as the target cell is the reported regeneration of fertile *Arabidopsis* plants from immature cotyledons in the absence of 2,4-D (Patton and Meinke, 1988). In addition, protocols have been described for the regeneration of fertile *Arabidopsis* plants from leaf explants, also in the absence of 2,4-D (Lloyd et al., 1986; Van der Graaff and Hooykas, 1996).

As described in Example III, *Arabidopsis thaliana* and *Brassica napus* belong to the same family, Cruciferae, and therefore the plastid genomes share a high degree of homology and the gene order is essentially identical (Palmer et al., 1994). Accordingly, plastid transformation vectors and expression cassettes developed for *Arabidopsis* can be used for plastid transformation and expression of foreign genes in *Brassica* species without modification. The following definitions are provided to facilitate an understanding of the present invention:

Heteroplasmic: refers to the presence of a mixed population of different plastid genomes within a single plastid or in a population of plastids contained in plant cells or tissues.

Homoplasmic: refers to a pure population of plastid genomes, either within a plastid or within a population contained in plant cells and tissues. Homoplasmic plastids, cells or tissues are genetically stable because they contain only one type of plastid genome. Hence, they remain homoplasmic even after the selection pressure has been removed, and selfed progeny are also homoplasmic. For purposes of the present invention, heteroplasmic populations of genomes that are functionally homoplasmic (i.e., contain only minor populations of wild-type DNA or, transformed genomes with sequence variations) may be referred to herein as "functionally homoplasmic" or "substantially homoplasmic. These types of cells or tissues can be readily purified to homoplasmy by continued selection on the selection medium. Most seed progeny of such plants are homoplasmic in the absence of selection pressure, due to random sorting of plastid genomes.

Chimeric: a nucleic acid molecule having sequences derived from different species.

Transgene: a nucleic acid molecule encoding at least one foreign gene of interest. Transgenes consisting of more than one coding regions operably linked to appropriate expression signals may encode one or more proteins.

Plastome: the genome of a plastid.

Transplastome: a transformed plastid genome.

Transformation of plastids: stable integration of transforming DNA into the plastid genome that is transmitted to the seed progeny of plants containing the transformed plastids.

Selectable marker: the term "selectable marker" refers to a phenotype that identifies a successfully transformed organelle, cell or tissue, when a gene or allele encoding the selectable marker is included in the foreign DNA used for transformation.

Transforming DNA: refers to homologous DNA, or heterologous DNA flanked by homologous DNA, which when introduced into plastids replaces part of the plastid genome by homologous recombination.

Targeting segment: refers to those homogologous flanking regions which facilitate homologous recombination between foreign DNA and the plastid genome.

Translationally fused: refers to two coding DNA segments within a construct derived from different sources spliced together in a construct such that a chimeric protein is expressed.

High auxin culture medium: plant tissue culture medium which contains auxin only, or a combination of high concentrations of auxin and very low concentrations of cytokinins. The response of a plant cell to an auxin is specific for a given taxonomic group. When different auxins are applied in combination, their effects may not be additive Furthermore, the tissue response to auxin may be modified by cytokinins. Accordingly, the type and concentration of auxin used should be determined empirically for the species to be transformed. A preferred example of a high auxin medium for use in the present invention is C1 medium, containing 1 mg/ml of the auxin 1-napthtaleneacetic acid (NAA) and a low concentration (0.2 mg/ml) of the cytokinin 6-benzylaminopurine (BAP). Other auxins, such as indole-3acetic acid (IAA) and dichloro-phenoxyacetic acid (2,4-D) may also be used to stimulate uniform cell division.

High cytokinin culture medium: like high auxin media, the response of plant cells to high cytokinin media is taxonomic group specific. An example of a preferred high cytokinin medium for use in the present invention is C medium, containing 1 mg/L of BAP, 2 mg/l of 2iP, (6-(gamma,gamma-Dimethylallyamino)purine or IPA, N6-(Isopentenyl)adenine) and a low concentration of the auxin NAA (0.1 mg/L) other cytokinins which may be used is 6-Furfurylaminopurine (KIN or kinetin).

The detailed description provided in the following examples relates to preferred methods for making and using the DNA constructs of the present invention and for practicing the methods of the invention. Any molecular cloning and recombinant DNA techniques not specifically described are carried out by standard methods, as generally set forth, for example in Sambrook et al., "DNA Cloning, A Laboratory Manual," Cold Spring Harbor Laboratory, 1989 or Ausubel et al. eds. in "Current Protocols in Molecular Biology", John Wiley and Sons, 1995. Materials, methods and vectors suitable for transforming plastids are disclosed in U.S. Pat. Nos. 5,451,513 and 5,877,402, the entire disclosures of which are incorporated herein by reference.

The following examples are provided to more fully describe the instant invention. They are not intended to limit the scope of the invention in any way.

EXAMPLE I

Plastid Transformation in *Arabidopsis* Leaves by Selection for Spectinomycin Resistance The following materials and protocols enable the practice of the methods of Example I. A schematic diagram of the methods utilized is provided in FIG. 2.

Plant Material

As the recipient for transformation, the *Arabidopsis* ecotype RLD was used. This ecotype has been reported to regenerate readily in culture (Marton and Browse, 1991).

Construction of Vector pGS31A

The *Arabidopsis* plastid transformation vector pGS31A is shown in FIG. 1. The immediate progenitor of pGS31A is plasmid pGS7, a pBluescript KS(+) phagemid vector (Stratagene) derivative. Plasmid pGS7 carries a 2-kb HindIII-EcoRI *Arabidopsis* ptDNA fragment containing the 5'-end of the 16S rRNA gene, trnV and part of the rps12/7 operon. During construction of the pGS7 plasmid, the HindIII site has been removed by digestion with HindIII (site in 16SrDNA) and KpnI (in vector, treated with the T4 DNA polymerase to remove the single-stranded overhangs) and ligating the blunt ends. Vector pGS31A carries the selectable spectinomycin resistance gene, (Prrn::aadA::TpsbA) present in plasmid pZS197 (Svab and Maliga, 1993). The aadA coding region is transcribed from a synthetic promoter consisting of the promoter of the tobacco rRNA operon fused with a synthetic ribosome binding site (Prrn). The aadA mRNA is stabilized by transcriptionally fusing sequences downstream of the coding region with the 3'-untranslated region of the tobacco plastid psbA gene (TpsbA). The gene in pGS31A derives from a modified progenitor of pZS197 in which the XbaI site between aadA and TpsbA was removed by blunting. Plasmid pGS31A was obtained by excising the chimeric aadA gene with Ec1136II (an isochisomer of SacI, yields blunt ends) and BspHI (single-stranded overhang filled in to obtain blunt ends) for ligation into the unique HincII site of plasmid pGS7 between trnV and the rps12/7 operon.

Tissue Culture Media

The tissue culture protocols were adapted from those of Marton and Browse (1991) and Czako et al. (1993). The *Arabidopsis* tissue culture media (ARM) is a derivative of the Murashige & Skoog (1962) MS medium. ARM medium: ms salts, 3% sucrose, 0.8% TC agar, 2 ml/L of the vitamin solution (100 mg myo-inositol, 5 mg vitamin B1, 0.5 mg vitamin B6, 0.5 mg nicotinic acid, 1 mg glycine and 0.05 mg biotin per ml). ARM1 medium: ARM medium containing 3 mg indoleacetic acid (IAA), 0.15 mg 2,4-dichlorophenoxyacetic acid (2,4-D), 0.6 mg benzyladenine (BA) and 0.3 mg isopentenyladenine (IPA) per liter. ARMIIr medium: ARM medium supplemented with 0.2 mg/L naphthaleneacetic acid (NAA) and 0.4 mg/L IPA. *Arabidopsis* shoot induction (ASI-N1B1) medium: ARM medium supplemented with 1 mg/L NAA and 1 mg/L BAP. The *Arabidopsis* shoots were rooted on ARM medium. *Arabidopsis* seed culture (ARM5) medium: ARM medium supplemented with 5% sucrose. The stocks of plant hormones were filter sterilized, and added to media cooled to 45° C. after autoclaving. Selective media contained 500 mg/L spectinomycin HCl and/or streptomycin sulfate. The antibiotics (filter sterilized) were added to media cooled to 45° C. after autoclaving.

Cultivation of *Arabidopsis* Plants in Sterile Culture

For surface sterilization, seeds (25 mg) were treated with 1 ml of commercial bleach (5.25% sodium hypochlorite) in an Eppendorf tube for 5-7 minutes with occasional vortexing. The seeds along with the bleach were poured into a 15 ml conical centrifuge tube containing 10 ml 90% ethanol and incubated for 5-7 minutes. The ethanol-bleach mix was decanted, and the seeds were washed 4 times with 10 ml autoclaved deionized water and finally resuspended in sterile water (approximately 150 seeds/ml). The resulting seed suspension (2 ml) was poured into 10 cm deep (10 mm high) petri dishes containing 50 ml ARM5 medium. The seeds were spread evenly by swirling the suspension. The water was then removed from the plates by pipetting. The seeds germinated after a 10-15 day incubation at 24° C. during which the plates were illuminated for 8 hours using cool-white fluorescent tubes (2000 lux).

To grow plants with larger leaves, seedlings were individually transferred to ARM5 plates (10 plants per 10 cm petri dish) and illuminated for 8 hours with cool-white fluorescent bulbs (lux; 21° C. day and 18° C. night temperature). The thick, dark green leaves, 1 cm to 2 cm in size, were harvested for bombardment after 5-6 weeks.

Transformation and Selection of Spectinomycin Resistant Lines.

Leaves (approximately 1.5 to 30 mm in length) for plastid transformation were harvested from aseptically grown plants. To cover a circular area 4 to 5 cm in diameter, 12 to 18 leaves were placed on agar-solidified ARMI medium. The pGS31A vector DNA was introduced into leaf chloroplasts by the biolistic process, on the surface of microscopic (1 μm) tungsten particles using a helium-driven PDS1000 biolistic gun. Fresh leaves were bombarded at 450 psi (target placed at 9 cm, from rupture disk; position No. 3 from top in the biolistic gun). Leaves cultured for 4 days on ARMI medium were bombarded at 1100 psi (target placed at 12 cm from rupture disk; position No. 4 from top in the biolistic gun).

Leaf bombardment was performed in ARMI medium. Following bombardment, the leaves were incubated for two additional days in ARMI medium. After this time period, the leaves were stamped with a stack of razor blades to create a series of parallel incisions 1 mm apart. It has been observed previously that mechanical wounding is essential to induce uniform callus formation in the leaf blades. The stamped leaves were transferred onto the same medium (ARMI) containing spectinomycin (500 mg/ml) to facilitate preferential replication of plastids containing transformed ptDNA copies. The ARMI medium induces division of the leaf cells and formation of colorless, embryogenic callus. After 7-10 day selection on ARMI medium, spectinomycin selection was continued on the ARMIIr medium which normally induces greening. Since spectinomycin prevents greening of wild-type cells, only spectinomcyin-resistant cells formed green calli. Visible green cell clusters on the selective ARMIIr medium appeared within 21 to 70 days.

In 201 bombarded samples, 19 spectinomcyin-resistant lines were obtained. Plant regeneration was attempted in 14 spectinomycin-resistant lines, and succeeded in 10 of them. Shoots from the green calli regenerated on the ASI-N1B1 medium, and were rooted on ARM medium.

Table 1 sets forth the recovery of spectinomycin resistant cell lines after biolistic delivery of plasmid pGS31A.

TABLE 1

Recovery of spectinomycin resistant lines after bombardment of *A. thaliana* with plasmid pGS31A

| DNA[1] | Number of Samples | psi[2] | Spc$^r$ | Plant | pt | Nucleus | Spont. mutant. |
|---|---|---|---|---|---|---|---|
| N/A | 100 | | 1 | 0 | | | 1 |
| pGS31A | 40 | 1100 | 8 | 6 | 1 | 7 | 0 |
| pSG31A | 151 | 450 | 11 | 8 | 1 | 10 | 0 |

[1]The control plates were not bombarded.
[2]psi = pounds per square inch, the value of rupture disk.

Southern Hybridization Analysis of Total Cellular DNA to Verify Plastid Transformation Spectinomycin resistance may be due to expression of aadA in plastids (Svab and Maliga, 1993), expression of aadA in the nucleus (Svab et al., 1990b), or spontaneous mutation (Fromm et al., 1987; Svab and Maliga, 1991). Southern hybridization was performed to identify plastid tranformants in the spectinomycin resistant lines isolated. Total cellular DNA was isolated according to Mettler (1987). Restriction enzyme-digested DNA was electrophoresed in 0.7% agarose gels and transferred to nylon membrane (Amersham) using the PosiBlot transfer apparatus (Stratagene). Blots were probed by using Rapid Hybridization Buffer (Amersham) with $^{32}$P labeled probes generated by random priming (Boehringer-Mannheim). When using the targeting ptDNA as a probe, in lines At-pGS31A-2 and At-pGS31A-16, the 3.82 kb transgenic fragment was the only fragment detected indicating that the wild-type ptDNA copies have been selectively diluted out during cell divisions on the selective medium. The same transgenic fragment also hybridized with the aadA probe (FIG. 1C).

Among the 19 spectinomycin resistant lines, 17 nuclear transformants were identified by a wild-type fragment on Southern blots when hybridizing with the targeting ptDNA probe. Note that the Southern blots used were optimized for the high-copy (10,000 per cell) leaf ptDNA and will not give a signal with a few nuclear aadA copies.

Spontaneous mutants are expected to have wildtype ptDNA targeting fragment on Southern blots and no PCR-amplifiable aadA gene. In the sample of 19 spectinomycin resistant lines, no such spontaneous mutant was found.

PCR Amplification of Inserted aadA Sequences

DNA was amplified according to standard protocols (1 min at 92° C., 1.5 min at 58° C., 1.5 min at 72° C., 30 cycles). Spectinomycin resistance resulting from aadA expression may be verified by PCR amplification of a 407 nucleotide internal segment using the following primers: 5'-GCTTGATGAAACAACGCGG-3' 5'-CCAAGCGATCT-TCTTCTTGTCCAAG-3'

Transplastomic *Arabidopsis* Plants

While the transplastomic *Arabidopsis* plants all flowered, none of them set seed after selfing, or after fertilization with pollen from wild-type plants. Included among these were 98 plants regenerated from the two lines in which spectinomcyin resistance was due to plastid transformation, and 66 plants regenerated from 12 lines in which spectinomcyin resistance was due to expression of aadA in the nuclear genome.

Conclusions and Implications

An important agricultural breakthrough, plastid transformation in the model species *Arabidopsis thaliana* is described in the instant invention. Based on the foregoing results, it has been found that a chimeric aadA gene, when inserted in the *Arabidopsis* ptDNA targeting cassette, was suitable to recover plastid transformants following biolistic delivery of the transforming DNA. However, the number of *Arabidopsis* plastid transformants was significantly lower, about one in 100, than anticipated based on the transformation of tobacco plastids which yields on average one transformant per bombarded sample (Svab and Maliga, 1993; Zoubenko et al., 1994).

There may be multiple reasons for the relatively low transformation efficiency. Inherent species-specific differences, such as relatively inefficient homologous rb-combination system in *Arabidopsis* chloroplasts could be one obvious reason.

In tobacco vector pZS197, aadA is flanked by 1.56-kb and 1.29-kb of ptDNA, and yields approximately 1 transformant per bombardment (Svab et al., 1993). In plasmid pRB15, also a tobacco vector, aadA is flanked by larger targeting segments, 1.56-kb and 3.6-kb of ptDNA, and yields approximately 5 plastid transformants per bombardment (Bock and Maliga, 1995). In *Arabidopsis* vector pGS31A aadA is flanked only by approximately 1-kb plastid targeting sequence on both sides. Therefore, the efficiency of plastid transformation in *Arabidopsis* may be significantly improved by increasing the size of the targeting ptDNA fragment.

In contrast to tobacco, in which most of the plants regenerated from leaves are fertile, it was surprising to find that none of the 164 regenerated *Arabidopsis* plants set seed. Lack of fertility, in part, may be due to the extensive polyploidy of leaf tissue as reported by Galbright et al., (1991) and Melaragno et al. (1993). An additional reason for lack of fertility may be the prolonged exposure of the cultures to 2,4 D (Van der Graaff and Hooykaas, 1996).

EXAMPLE II

Plastid Transformation in *Arabidopsis* Cotyledons by Selection for Kanamycin Resistance Plastid transformation has been obtained in *Arabidopsis thaliana* by selection for spectinomycin resistance in leaf cultures following bombardment with DNA-coated tungsten particles, as set forth in Example I. While plastid transformation has been successful, the regenerated plants were not fertile. These obstacles have been overcome by altering certain parameters of the transformation protocol.

The protocol developed and set forth in this Example has the following salient features: (1) Cotyledons obtained by germinating mature seed are used to advantage because of their ready availability, and the ease by which large quantities of sterile cotyledons are obtained from surface-sterilized seed. (2) The protocol has two distinct steps. The first step employing a high auxin medium to induce uniform cell division throughout the cotyledon (Stage I) and the second step including a high cytokinin medium to induce plant regeneration (Stages II and III). The protocol was designed to either minimize exposure to medium containing 2,4-D during tissue culture, or more preferably to eliminate such exposure completely. (3) Initial culturing of the cotyledon cells at a high density, i.e., 500-200 cotyledons/20 ml in liquid culture medium during the first 8 days (Stage I, II) proved essential for obtaining abundant plant regeneration later.

Figure 4:
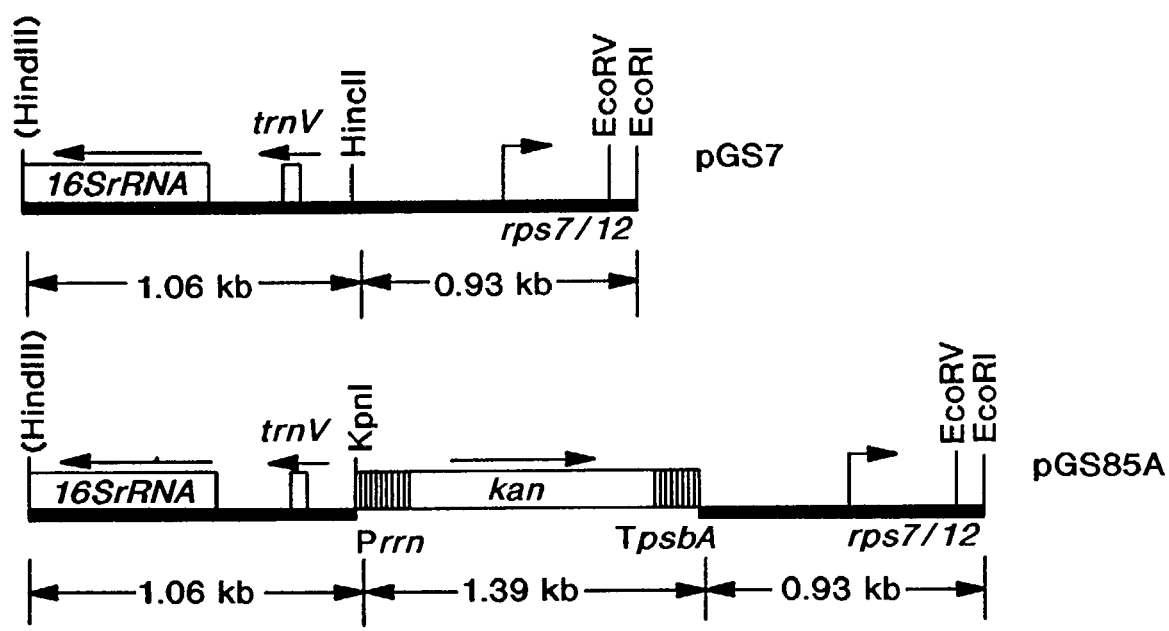
FIG. 4 is a map of the plastid targeting region of pGS7 and pGS85A plasmids. Note unique HincII cloning site in plasmid pGS7 and KpnI restriction site in plasmid pGS85, and chimeric kan kanamycin resistance gene. The plastid genes trnV, 16SrDNA and rps12/7 are described in Shinozaki et al., 1986. Site and direction of transcription initiation is indicated by horizontal arrow.
Figure 7:
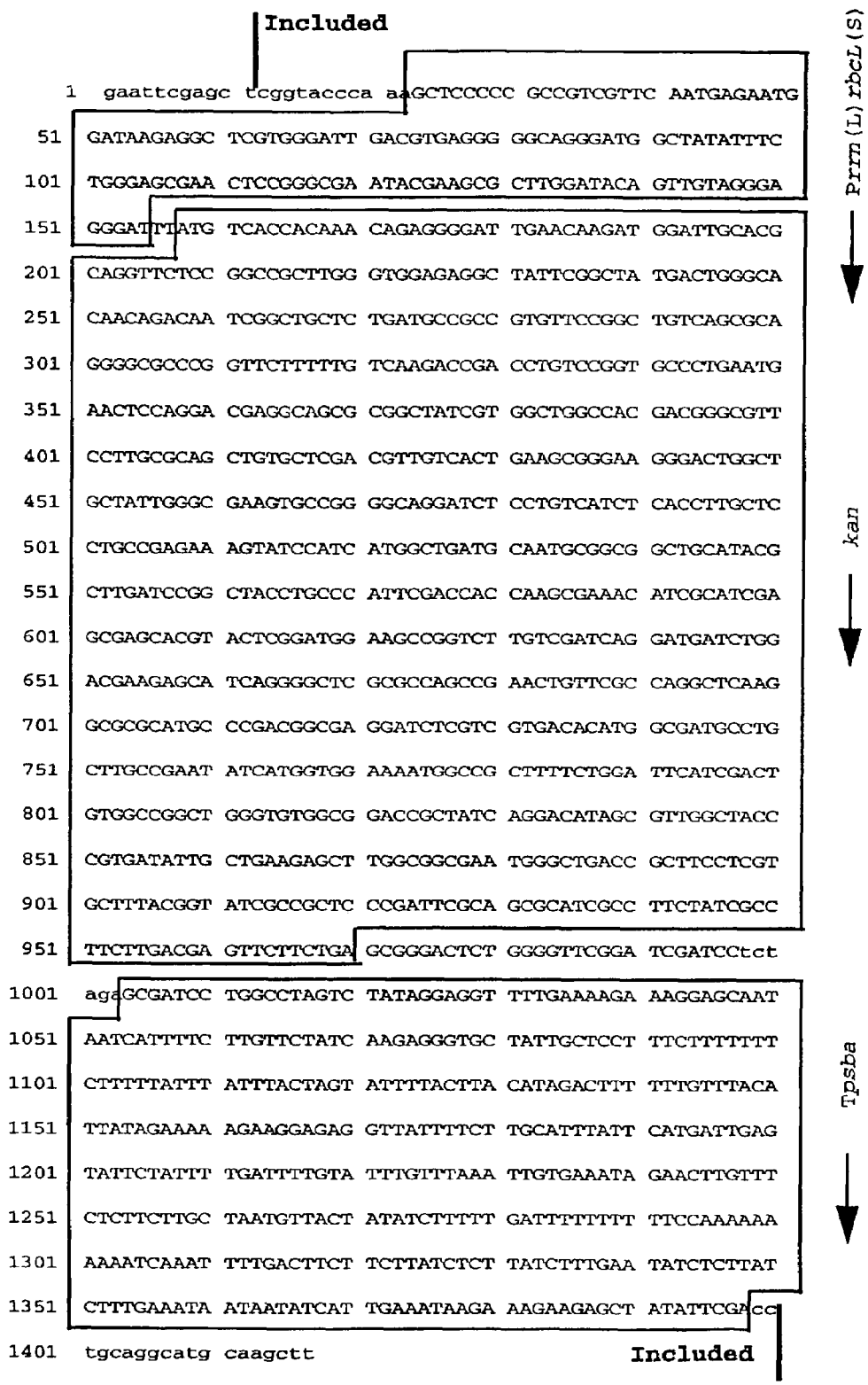
FIG. 7 is the sequence of the plastid targeting region (SEQ ID NO: 3) of plasmid pGS85A.

The protocol for plastid transformation in *Arabidopsis* utilizing cotyledons as target tissue and kanamycin-resistance as a selective marker was implemented as follows. The chimeric kan gene derives from plasmid pTNH7, a pUC118 derivative encoding neomycin phosphotransferase (NPTII), an enzyme which enzymatically inactivates the kanamycin antibiotic. The same chimeric kan gene in a tobacco targeting plasmid (plasmids pTNH32) was used for direct selection of plastid transformants in tobacco (Carrer et al. 1993). The construction of the kan gene was described in more detail in this same reference. Plasmid pGS85A was obtained by excising kan from pTNH7 as a SacI/PstI fragment, blunting, and cloning the fragment into the HincII site of plasmid pGS7 (FIG. 4). The kan gene in pGS85A, as aadA in plasmid pGS31A, is expressed in a Prrn/TpsbA cassette. However, the five N-terminal amino acids of the highly-expressed rbcL coding region were translationally fused with the neomycin phosphotransferase-terminus. This translational fusion in tobacco lead to the accumulation of NPTII at 10× higher levels than from identical, constructs without the rbcL-terminal segment. The DNA sequence of pGS85A, including that of the chimeric kan gene, is set forth herein.

Initially, seed-set was tested in plants regenerated via the tissue culture protocol. Selection of kanamycin resistant clones after bombardment with DNA-coated tungsten was subsequently assessed. These improvements to the method are suitable for the generation of fertile, transformed *Arabidopsis* plants. The following material and protocols were utilized in practicing the methods of this Example II.

Seed Germination

Seeds of *Arabidopsis thaliana* ecotype RLD are surface sterilized using commercial bleach (5% sodium hypochlorite) for 5 minutes followed by a subsequent 5 minute treatment with 95% ethanol. A drop of Triton X-100 was added to the bleach to wet the surface of the seeds during the sterilization period. After sterilization, seeds were washed 5-6 times with sterile deionized water. Seeds were germinated on GM medium in 10 cm Petri dishes. See Table 2. The Petri dishes were incubated for 8 to 9 days in a Percival growth chamber at 23° C. under continous light.

TABLE 2

Composition of seed germination (GM) medium.

| Medium | Concentration (mg/L) |
| --- | --- |
| MS basal salts | 0.5X |
| myo-inositol | 100 |
| Thiamine | 0.1 |
| Pyridoxine | 0.5 |
| Nicotinic acid | 0.5 |
| Glycine | 2.0 |
| Sucrose | 30 g/L |
| pH | 5.8 |

Reference: van der Graaff and Hooykaas, 1996.

Tissue Culture Media and Culture Conditions

Compositions of the tissue culture media used for Stages I, II and III of the selection protocol are listed in Tables 2 and 3. Stage I and Stage II liquid cultures were established by aseptically transferring at least 50 to 2000 cotyledons to a Petri dish (100 mm×20 mm), each dish containing approximately 20 ml of medium. The Petri dishes were incubated at 23° C. on a New Brunswick G10 gyrotory shaker at 60 rpm and illuminated for 16 hours with cool fluorescent-light. In the Stage III protocol, cotyledons were incubated on agar-solidified (0.8% TC agar, JRH Biosciences) media at approximately 25-30 cotyledons per Petri dish (100 mm×20 mm) in 50 ml of media. The cultures were illuminated as described for Stages I and II.

Regenerated plants were directly transferred to GM medium in Magenta boxes with vented lids for gas exchange. Plants in the Magenta boxes were incubated in the culture room at 23° C., and illuminated for 16 hours with cool fluorescent light. The plants flowered and set seeds in the boxes.

The methods described for Example I were modified to generate fertile *Arabidopsis* plants having transformed plastid genomes. Three distinct tissue culture stages were employed to obtain plastid transformation. Stage I: liquid culture, in high auxin medium to stimulate uniform cell division. Stage II: liquid culture, in high cytokinin medium to induce plant regeneration from the transformed cells. Stage III: culture on agar-solidified medium, containing high levels of cytokinins also to induce plant regeneration.

Figure 3:
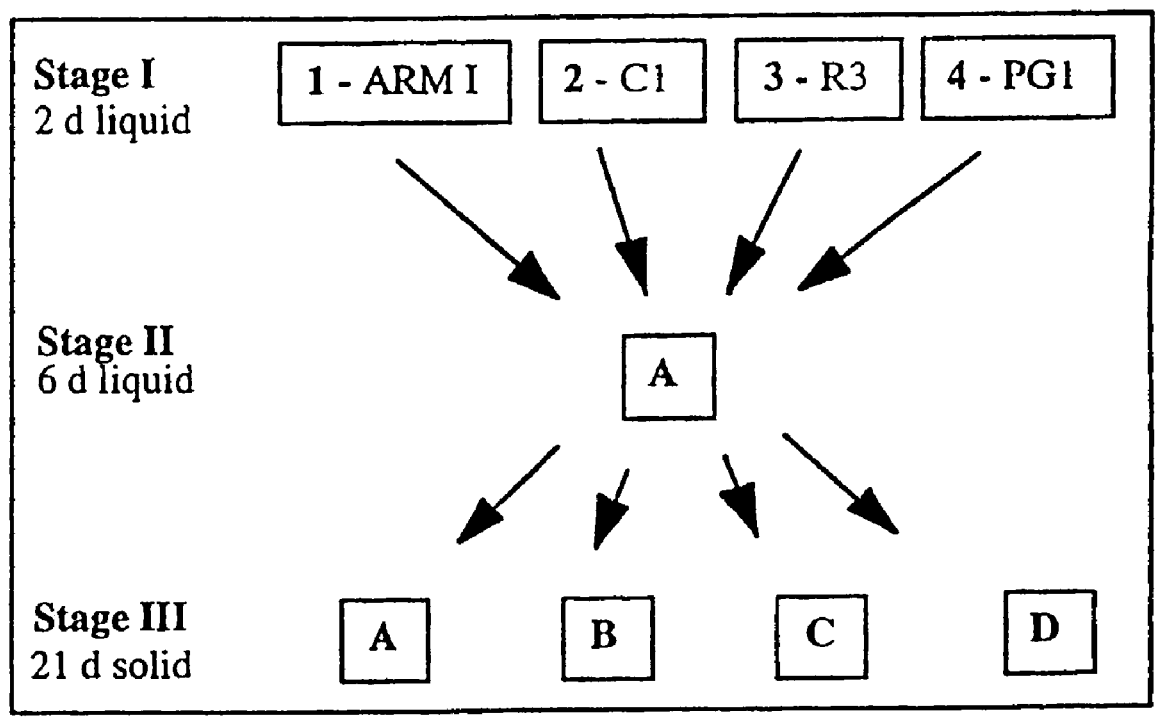
FIG. 3 is a schematic diagram of the different protocols used for obtaining fertile *Arabidopsis* plants from cotyledonary explants of *Arabidopsis thaliana* (RLD) having transformed plastids.

A schematic diagram of the strategy used to identify the best protocol for obtaining fertile plastid transformants is outlined in FIG. 3. To induce uniform cell division in liquid culture, four media, C1 (van der Graaff and Hooykaas, 1996), ARM I (Marton and Browse, 1991), R3 and PG1 (Feldmann and Marks, 1986; reported to induce callus and/or somatic embryogenesis in *Arabidopsis*) were utilized. Stage I treatment was kept short (2 days) to adopt to the usual timing of transferring the explants to a selective medium after bombardment, and to minimize the adverse effect of 2-4-D, if used at all. The composition of the Stage I tissue culture media utilized is set forth in Table 3 below.

TABLE 3

Composition of stage I tissue culture media*.

| Media | ARM I | C1 | R3 | PG1 |
| --- | --- | --- | --- | --- |
| Basal salts | MS | MS | MS | MS |
| Vitamins | ARM I | B5 | MS | B5 |
| 2,4-D | 0.15 | — | 0.5 | 2.2 |
| BAP | 0.6 | 0.2 | — | — |
| IAA | 3.0 | — | 5.0 | — |
| IPA | 0.3 | — | — | — |
| NAA | — | 1.0 | — | — |
| KIN | — | — | 0.3 | 0.05 |
| Sucrose | 30 g | 30 g | 30 g | 30 g |
| pH | 5.8 | 5.8 | 5.8 | 5.8 |

*All components are in mg/L. References: ARMI, Marton and Browse, 1991; C1, van der Graaff and Hooykaas, 1996; R3 and PG1, Feldmann and Marko (1986).

For Stage II culture, only one medium (A; Table 4) was used. This medium was efficient for inducing plant regeneration from immature cotyledons (Patton and Meinke, 1988). The cotyledons at Stage II were kept for a total of 6 additional days at high density in liquid culture.

For Stage III culture, the cotyledons were transferred to four types of agar-solidified regeneration media. These include the A medium developed for plant regeneration from immature embryos (Patton and Meinke, 1988); the B medium developed for plant regeneration from root explants (ARMII; Marton and Browse, 1991); the C medium that designed herein; and the D medium which is an embryo-induction medium for roots (ARMI; Marton and Browse, 1991) and leaf explants (Example I).

TABLE 4

Stage II and stage III plant regeneration media.

| Media | A medium* | B medium* | C medium* | D medium* |
|---|---|---|---|---|
| Basal salts | MS | MS | MS | MS |
| Vitamins | B5 | B5 | B5 | B5 |
| NAA | 0.1 | — | 0.1 | — |
| IAA | — | 0.1 | — | 3.0 |
| BAP | 1.0 | — | 1.0 | 0.6 |
| 2iP | — | 4.0 | 2.0 | 0.3 |
| 2,4-D | — | — | — | 0.15 |
| Sucrose | 30 g | 30 g | 30 g | 30 g |
| Agar (TC) | 7 g | 7 g | 7 g | 7 g |
| pH | 5.8 | 5.8 | 5.8 | 5.8 |

*All components are in mg/L. A medium is based on Patton and Heinke, 1988; B medium is the same as ARMII in Marton and Bowse, 1991; C medium developed herein, based on A and D media; D medium is the same as ARMI embryo-induction medium in Marton and Browse, 1991.

Plant Regeneration and Testing of Fertility

Cotyledons remained green and slightly expanded in size during the first 2 days of culture at Stage I in all four media. After 2 days in callus/embryo induction medium, cotyledons for Stage II were transferred from all four media to the A liquid regeneration medium. Green callus started appearing after 3 days of culture in A medium and by the 7th day callus appeared all over the cotyledons. At this stage cultures were transferred to the semi-solid media of Stage III which promotes embryo/shoot growth. Calli derived from media 1 (ARM1) and 2 (C1) were green. Development of plantlets from these explants could be seen by 21 days of culture. Callus derived from media 3 (R3) and 4 (PG1) was also green but very compact. This is probably due to the high concentration of 2,4-D in the Stage I media. A few plantlets in these cultures appeared only after 30 days. Plants from all cultures were transferred to hormone free GM medium as soon as they were 5-10 mm in size.

The protocols diagrammed in FIG. 3 were evaluated at two levels: uniform induction of cell division and shoot regeneration from the cotyledons; and by production of viable seed on the regenerated plants. The results are summarized in Table 5. Based on the first criterion, the best combination was 2AC, that is C1 medium at Stage I and C medium at Stage III, these treatments resulted in prolific shoot regeneration which was observed on each of the explants. The second best combination was 1AC (35 out of 40 explants regenerating shoots), with ARM1 at Stage I and medium C at Stage III. Combinations with media 3 and 4 at Stage I performed very poorly, with only a very small fraction of cotyledons forming shoots.

As to formation of viable seed, with one exception each of the regenerated plants produced viable seed. See Table 5. Most importantly, no adverse effect on fertility was found in the two combinations (2AC and 1AC) in which shoot regeneration is prolific.

TABLE 5

Seed-set in Magenta boxes on Ara.bidopsis thaliana RLD plants regenerated via plastid transformation protocols schematically shown in FIG. 3.

| Media | Number of cotyledons cultured | Number of cotyledons with shoots | Number of plants in boxes | Number of with viable seed |
|---|---|---|---|---|
| 1AA | 40 | 20 | 8 | 8 |
| 1AB | 40 | 25 | 8 | 8 |
| 1AC | 40 | 35 | 8 | 8 |
| 1AD | 40 | — | — | — |
| 2AA | 40 | 25 | 12 | 12 |
| 2AB | 40 | 22 | 8 | 7 |
| 2AC | 40 | 40 | 16 | 16 |
| 2AD | 40 | 2 | — | — |
| 3AA | 40 | 12 | 4 | 4 |
| 3AB | 40 | 6 | 4 | 4 |
| 3AC | 40 | 20 | — | — |
| 3AD | 40 | 1 | — | — |
| 4AA | 40 | 1 | — | — |
| 4AB | 40 | 1 | — | — |
| 4AC | 40 | 4 | 4 | 4 |
| 4AD | 40 | 1 | — | 1 |

Selection of Plastid Transformants by Kanamycin Resistance

Expression of kan encoding neomycin phosphotrasferase (NPTII) confers resistance to kanamycin when introduced into the *Arabidopsis* nucleus. Engineered forms of kan have been extensively used to obtain nuclear transformants in *Arabidopsis*, see Valvekens et al., 1988, and *Brassica*, see Radke, et al., 1992. The kan gene has been converted into a plastid marker for the selection of plastid transformants in tobacco (Carrer et al., 1993). As set forth in Example I, *Arabidopsis* plastid transformants have been obtained by selection for spectinomycin resistance conferred by aadA in the tobacco Prrn/TpsbA cassette. Prrn is a promoter derived from the plastid rRNA operon and TpsbA contains the plastid psbA gene 3' untranslated region required for the stabilization of chimeric plastid mRNAs (Svab and Maliga, 1993). A kanamycin resistance marker gene suitable for the selection of plastid transformants may be obtained by expressing kan in the Prrn/TpsbA cassette. A suitable kanamycin resistance plastid transformation vector from *Arabidopsis* and *Brassica* is the pGS85A vector which carries the chimeric kanamycin gene from plasmid pTNH32 (Carrer et al. 1993). The insertion site in pGS85A is the Hinc II site in the trnV/rps12/7 intergenic region. However, other intergenic regions in the plastid genome may be targeted as long as the introduced transgene does not interfere with the expression of the flanking plastid genes.

Plastid transformation may be carried out following the 1AC or 2AC tissue culture protocols outlined above. To prepare a suitable target tissue for transformation, cotyledons from 8-9 day old seedlings are cut from seedlings in liquid ARM and C1 media and cultured for two days as dictated by the 1AC and 2AC protocols (FIG. 3). After two days the cotyledons are transferred to filter paper (Whatman No. 4) on agar-solidified non-selective medium of identical composition. Approximately 50 to 70 cotyledons are required to cover a 3 $CM^2$ area. The cotyledons are then bombarded with plasmid pGS85A, a transforming, kanamycin resistance, *Arabidopsis* vector. Plasmid preparation, coating of tungsten particles and bombardment are carried out as described for tobacco (Maliga, 1995). For phenotypic expression, the cotyledons may be left in the same plates for two days. Subsequently, the cotyledons may be transferred to a selective liquid A medium containing 50 mg/L kanamycin sulfate and cultured for an additional seven days. After 7 days, cotyledons are transferred to a selective, agar-solidified C medium containing 50 mg/L kanamycin. In an alternative embodiment, selection may be carried out initially using kanamycin at 25 mg/ml. At later stages of culture, the kanamycin concentration is increased to 50 mg/ml. Callus growth from the transformed cells on the selective medium may be observed as early as one week. However, additional kanamycin-resistant clones may appear for several more weeks. Some of these are plastid transformants, while others acquire resistance to kanamycin due to the expression of the plastid kan gene in the nucleus (Carrer et al., 1993). The two classes of kanamycin-resistant clones can be readily distinguished DNA gel blot analysis and PCR analysis (as described in Example I). DNA was amplified according to standard protocols (1 min at 92° C., 1.5 min at 58° C., 1.5 min at 72° C., 30 cycles). Kanamycin resistance occurs as the result of neomycin phosphotransferase gene expression which may be verified by PCR amplification of a 548 nucleotide internal segment using the following primers: 5'-CCGACCTGTCCGGTGCCC-3' 5'-CACGAC-GAGATCCTCGCCG-3'.

EXAMPLE III

Plastid Transformation in *Brassica napus* Leaves by Selection for Resistance to Spectinomycin and Kanamycin Given their essentially identical genomes, plastid transformation vectors and expression cassettes developed for *Arabidopsis* can be used to advantage for plastid transformation and expression of foreign genes in *Brassica* species without modification.

Certain plastid expression signals derived from evolutionarily distant species function in *Arabidopsis* and *Brassica* plastids. This observation is supported by the results described in Example I demonstrating that the tobacco Prrn/TpsbA cassette can be used for expressing the selectable spectinomycin resistance gene (aadA) in *Arabidopsis* plastids. However, not every tobacco expression signal functions properly in *Arabidopsis*. Studies with a vector identical to pGS31A, except that the termination signal TpsbA, has been replaced with signal Trps16 has a dramatic effect on obtaining plastid transformants. This plasmid gene was obtained by inserting the Prrn/Trps16 cassette into targeting site in the pGS7 vector. See FIG. 4. Zero plastid transformants were obtained out of 416 samples bombarded with this plasmid. As mentioned above, when a Prrn/TpsbA cassette (cassettes described in Staub and Maliga, Plant Journal 6: 547-553, 1994 and Svab and Maliga, 1993, the subject matter of which is incorporated herein by reference) was utilized to transform *Arabidopsis* leaves, plastid transformants were obtained, 2 out of 210 samples bombarded.

Due to their taxonomic relatedness, *Arabidopsis* and *Brassica* species respond similarly in tissue culture to plant hormones or to antibiotics. As a result, plant regeneration from cultured cells and selection of transgenic lines by antibiotic resistance may be accomplished by essentially the same protocol. Both *Arabidopsis* and *Brassica* leaf or cotyledon explants respond to 500 mg/L spectinomycin with prolific callus growth in wild-type, non-transformed tissue on shoot regeneration medium, such as medium C described in Table 6. This response differs significantly in tobacco leaf tissue wherein exposure to 500 mg/ml of spectinomycin results in a severe inhibition of callus proliferation on shoot induction medium. Thus, tobacco plastid (and nuclear gene) transformants can be readily regenerated on a shoot induction medium containing spectinomycin at 500 mg/L (Svab and Maligam 1993). Unfortunately, rapid callus proliferation on spectinomycin-containing C shoot/embryo regeneration medium (see table 6) prevents the recovery of *Arabidopsis* and *Brassica* plastid transformants. Culture conditions must be improved to suppress rapid callus growth to facilitate the recovery of plastid transformants. Such conditions are outlined in Example I. While selection was feasible and plastid transformants were obtained using the methods of Example I, the transplastomic plants generated were not fertile. However, given the higher tolerance of *Brassica* to 2,4 D (Radke et al., 1992) the same protocol described in example I may be adapted for use in *Brassica*.

The data presented in Example II indicate that kanamycin selection is compatible with the regeneration protocols described. Accordingly, kanamycin is the favored antibiotic for the selection of plastid transformants in the Cruciferae taxonomic group.

Examples I and II disclose protocols for the regeneration of transgenic plants from *Arabidopsis* leaves and cotyledons. A protocol for the regeneration of transgenic plants in *Brassica* would involve a two-stage protocol (application of two different media) for leaves, and a three-stage protocol (application of three different media) for cotyledons. The three-stage protocol described for use in the plastid transformation of *Arabidopsis* cotyledons in Example II is suitable for use in *Brassica*. Accordingly only the methods for transforming *Brassica* leaf plastids in a two stage process will be described below.

Plastid Transformation in *Brassica* Utilizing Leaves as Target Tissue and Kanamycin Resistance as the Selective Marker

*Brassica* Stage I culture results in the uniform induction of cell division in leaves or cotyledons. The objective of Stage II is regeneration of transgenic plants. A suitable Stage I medium for the induction of cell division would be the ARMI medium discussed in Examples I and II. Suitable Stage II regeneration media would be the B medium (ARMII in Marton and Browse, 1991), C medium (this study) and E medium (Pelletier et al. 1983) listed in Table 6.

TABLE 6

| Stage II Brassica plant regeneration media* | | | |
|---|---|---|---|
| Media | B medium | C medium | E medium |
| Basal salts | MS | MS | MS |
| Vitamins | B5 | B5 | B5 |
| NAA | — | 0.1 | 1.0 |
| IAA | 0.1 | — | — |
| BAP | — | 1.0 | — |
| 2iP | 4.0 | 2.0 | 1.0 |
| GA3 | — | — | 0.02 |
| Sucrose | 30 g | 30 g | 30 g |
| Agar (TC) | 7 g | 7 g | 7 g |
| pH | 5.8 | 5.8 | 5.8 |

*All components are in mg/L. B medium is the same as ARMII in Marton and Bowse, 1991; C medium is this study; E medium is the cruciferae regeneration medium of Pelletier et al. 1983.

For selection of plastid transformants, *Brassica napus* cv. Westar seeds should be surface sterilized, and germinated aseptically in Magenta boxes as described for *Arabidopsis* in Example II. After three to four weeks, the leaves are harvested, and directly placed on a Whatman filter paper placed on agar-solidified non-selective Stage I medium. Following bombardment with DNA of the appropriate plastid transformation vector carrying a selectable kanamycin-resistance marker, as described in Example II, the plates are incubated for two days in the light (16 hours) at 25° C. After 2 days the leaves are incised with a stack of sterile razor blades, and transferred to the same Stage I medium supplemented with 50 mg/L of kanamycin sulfate. In an alternative embodiment, selection may be carried out initially using kanamycin at 25 mg/ml. At later stages of culture, the kanamycin concentration is increased to 50 mg/ml. After two weeks on the selective Stage I medium, the leaves are transferred to one of the Stage II media for plant regeneration. Kanamycin resistant clones are identified by their rapid growth and shoot regeneration on the selection medium. Kanamycin resistance may be due to plastid transformation or integration of the kanamycin marker gene into the nuclear genome. Plastid transformation is verified by PCR and DNA gel blot analysis in tissue samples taken from kanamycin-resistant calli and regenerating shoots. The regenerated shoots are then rooted and transferred to soil in the greenhouse following standard protocols.

Example IV

Plastid Transformation in *Lesquerella fendleri*, an Oilseed Brassicacea

A plastid transformation protocol has also been developed in *Lesquerella fendleri*, a wild oilseed species of the Brassicaceae family with a high capacity for plant regeneration in tissue culture. Plastid transformation vector pZS391B carries a selectable spectinomcyin resistance (aadA16gfp) gene targeted for insertion in the trnV/rps12/7 intergenic region. Transforming DNA was introduced into *Lesquerella* leaves by the biolistic process. Spectinomycin prevented greening of non-transformed cells. Transplastomic clones were identified by their ability to form green shoots on the selective medium (400 mg/L spectinomcyin HCl). The transplastomic clones were also resistant to streptomycin, a characteristic of clones expressing aadA. Selection in 51 bombarded samples yielded 2 transplastomic clones. Fertile plants and seed progeny were obtained in transplastomic clone Lf-pZS391B-1.

In the same samples, 108 spontaneous mutants were identified. Spontaneous mutants, unlike the transformed clones, were resistant only to spectinomycin. Spectinomcyin resistance in four of the spontaneous mutants was localized to the 16S rRNA gene by the loss of a conserved AatII site. High regeneration potential in tissue culture is believed to be important for efficient plastid transformation. Although *Lesquerella* has a high regeneration potential, we report here plastid transformation efficiencies similar to those in *Arabidopsis*, a species with poor morphogenetic capacity. Thus, it appears that competence for plastid transformation in the oilseed Brassicacea *Lesquerella fendleri* is not linked to regeneration capacity.

Plastid transformation in non-tobacco species is much less efficient than that reported in tobacco. It has been hypothesized, that lower plastid transformation efficiency could be due to inefficient regeneration of plants from cultured cells (Sidorov et al. 1999). *Lesquerella fendleri* is a plant with a desirable seed oil composition making it a candidate for commercial production. The capacity for plant regeneration from cultured cells of *Lesquerella* is comparable to the morphogenic response of tobacco (Skarzhinskaya et al. 1996).

Both *Arabidopsis thaliana* and *Lesquerella fendleri* belong to the mustard family (Brassicaceae). In accordance with the present invention, experiments have been performed to determine if the high morphogenetic potential in *Lesquerella* may be correlated with competence for plastid transformation. The data reveal that plastid transformation efficiency is similar in *Lesquerella* and *Arabidopsis*. Thus, competence for plastid transformation does not appear to be linked to regeneration potential, at least not in the oilseed Brassicacea *Lesquerella fendleri*.

The following materials and methods are provided to facilitate the practice of the present invention as described in Example IV.

Construction of Vector PZS391B

Plastid transformation vector pZS391B is a pUC119 plasmid derivative lacking a ScaI site in the flanking vector sequence and targets insertions into the trnV-rps12/7 intergenic region of the *Lesquerella* plastid genome. The plasmid is a modified version of the *Arabidopsis* plastid vector pGS31A shown in FIG. 1 (Sikdar et al. 1998). Part of the left targeting region containing the 16S rRNA gene derives from the tobacco plastid genome (EcoRI-SphI fragment, at nucleotides 138540 and 139818 in the tobacco plastid genome; GenBank Accession No. Z00044). The rest of the left targeting region derives from the *Arabidopsis* plastid genome (SphI-HincII fragment, at nucleotide positions 137590 and 138094 in the *Arabidopsis* plastid genome; GenBank Accession No. AP000423). The selectable marker gene aadA16gfp utilized in this example encodes aminoglycoside 3'-adenyltransferase translationally fused via a 16-mer linker with the *Aequorea victoria* green fluorescent protein (Khan and Maliga 1999). The aadA16gfp gene is expressed in an expression cassette consisting of a modified tobacco plastid rRNA operon promoter PrrnLrbcL (Kuroda and Maliga 2000) and the 3' untranslated region of the plastid psbA gene (TpsbA)(Khan and Maliga 1999). The right targeting region is comprised of a HincII-XbaI *Arabidopsis* plastid DNA fragment (restriction sites at nucleotides 138094 and 138943; GenBank Accession No. AP000423). DNA sequence of plasmid pZS391B plastid targeting region has been deposited in GenBank (GenBank Accession No. not yet assigned). To obtain plasmid pZS391B, the chimeric aadA16gfp gene was cloned as an EcoRI-HindIII fragment into a BluescriptII KS+ vector, then excised as a SmaI-HincII fragment and ligated into HincII digested pZS344.

Plastid Transformation

*Lesquerella fendleri* (Gray) Wats seed (A 14581) was obtained from the USDA Western Regional Plant Introduction Station, Pullman, Wash. The plants were grown aseptically on hormone free C1 medium, which is a modified MS medium (Van der Graaff and Hooykaas 1996) at 24° C., and illuminated for 16 hours a day. Leaf segments (10 to 15 mm) were harvested from six-week old plants. For bombardment, 10 to 12 leaf segments were placed on a filter paper abaxial side up on C2 medium (C1 medium containing 1 mg L$^{-1}$ BA and 0.1 mg L$^{-1}$ NAA). Leaf segments were bombarded with tungsten particles (M–10; 0.6 to 0.9 µm) coated with pZS391B plasmid DNA (DuPont PDS1000He Biolistic gun; 1100 p.s.i.)(Maliga 1995). Two days after bombardment the leaves were cut into smaller pieces (5 mm long), dissected longitudinally to yield 2-mm wide strips and placed on C2 medium containing 400 mg L$^{-1}$ spectinomycin HCl. The leaf segments were subcultured to the same selective medium at 14 to 20 day intervals. Spectinomycin resistant clones appeared in 5 to 7 weeks, identified as green shoots on bleached sensitive leaf segments. Transplastomic clones were identified on a C2 medium by testing leaf segments for resistance to both spectinomycin HCl (200 mg L$^{-1}$) and streptomycin sulfate (200 mg $L^{-1}$). Subclones of transplastomic clones were established by rooting spectinomycin-streptomycin resistant shoots on drug-free C1 medium, and were distinguished by capital letters. The subclones were further purified by a second cycle of shoot regeneration on C2 medium containing 400 mg $L^{-1}$ spectinomycin HCl.

Southern Analysis of Total Cellular DNA

Total leaf cellular DNA was extracted (Mettler 1987), digested with the appropriate restriction enzyme and separated in 0.8% or 1% agarose gels (0.5 µg to 2 µg per lane). After separation, the DNA was transferred to nylon membranes (Amersham) using the PosiBlot transfer apparatus (Stratagene). The blots were probed using Rapid Hybridization Buffer (Amersham) with ($^{32}$P)-dCTP labeled probes generated by random priming (Pharmacia). The targeting region in the transformed plants was probed with two plastid DNA fragments containing the 16S rRNA gene: the wild-type HindIII-EcoRI *Arabidopsis* fragment (P2; GenBank Accession No. AP000423) and the wild-type EcoRI-HincII tobacco plastid DNA fragment (P3, GenBank Accession No. Z00044). Incorporation of aadA in the plastid genome was verified using an NcoI/XbaI fragment (P1 probe) (Sikdar et al. 1998).

Detection of GFP by Fluorescence Microscopy

Subcellular localization of GFP was verified by laser-scanning confocal microscopy (Sarastro 2000 Confocal Image System, Molecular Dynamics, Sunnyvale, Calif.). This system utilizes an argon mixed gas laser with lines at 488 and 568 nm and detector channels. The channels are adjusted for fluorescein and rhodamine images. GFP fluorescence was detected in the FITC channel (488-514 nm). Chlorophyll fluorescence was detected in the TRITC channel (560-580 nm). The images produced by GFP and chlorophyll fluorescence were processed using the Adobe PhotoShop software.

Results

Transformation vectors utilizing tobacco plastid targeting sequences are available (Zoubenko et al. 1994). To minimize potential incompatibility problems, we developed plastid vectors with homologous targeting sequences for the Brassicaceae family. *Lesquerella* and *Arabidopsis* belong to this family, therefore we utilized the available *Arabidopsis* plastid targeting regions. *Arabidopsis* vector pGS7 has a short targeting segment (Sikdar et al. 1998).

In accordance with the present invention, a new plastid vector for Brassicaceae species has been developed. This plastid vector contains enlarged targeting sequences to facilitate integration. Additionally, HindIII, StuI and XbaI restriction sites have been removed to facilitate DNA manipulations in *E. coli*. The XbaI site was removed by deleting the terminal 96 nucleotides from the *Arabidopsis* right targeting region. The HindIII and StuI sites fall within rrn16 (16S rRNA gene). The HindIII and StuI sites in the left targeting region were removed by replacing the *Arabidopsis* rrn16 sequence with the tobacco rrn16 sequence. The rrn16 coding sequence is highly conserved between tobacco and *Arabidopsis*; there are only eight point mutations in the 1.3-kb EcoRI-SphI fragment. Therefore, replacement of the *Lesquerella* rrn16 with the tobacco rrn16 was not expected to impair plastid function. In contrast, sequences outside the rrn16 region are highly divergent between tobacco and *Arabidopsis* containing several large deletions, insertions and numerous point mutations. The final product, pZS344, has 1.8-kb and 0.9-kb targeting regions and is a backbone for Brassicaceae-specific plastid vectors (FIG. 8A). Plastid vector pZS391B was obtained by ligating aadA16gfp into the HincII site. The aadA16gfp gene encodes aminoglycoside 3'-adenyltransferase translationally fused via a 16-mer linker with the *Aequorea victoria* green fluorescent protein. The fusion protein confers resistance to spectinomycin and streptomycin when expressed in chloroplasts (Khan and Maliga 1999).

Transplastomic *Lesquerella fendleri* Clones

Figure 9A:
FIG. 9A, Selection for spectinomycin resistance in bombarded leaf culture. Arrows point to resistant shoot and callus.

Transformation vector pZS391B was introduced into chloroplasts on the surface of tungsten particles by the biolistic process. The leaf sections were incubated on drug-free medium for two days, then transferred to a selective C2 medium containing spectinomycin (400 mg $L^{-1}$). *Lesquerella* leaf segments on C2 medium form green shoots on the entire leaf surface. Spectinomycin in the C2 medium in the range of 50 mg $L^{-1}$ to 400 mg $L^{-1}$ prevents shoot regeneration and induces formation of non-pigmented (yellow) callus on the leaf sections. Spectinomycin resistant clones were identified as green shoots or green calli (FIG. 9A). From 51 bombarded plates, 110 spectinomycin resistant clones were obtained.

Figure 9B:
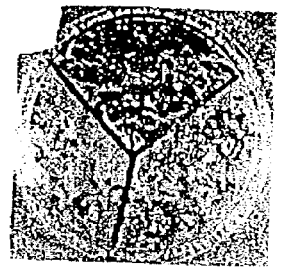
FIG. 9B, Identification of transplastomic clones by resistance to streptomycin (200 mg $L^{-1}$) and spectinomycin (200 mg $L^{-1}$). Note one resistant (green) and two sensitive (yellow) clones.

Transplastomic clones expressing aadA16gfp and spontaneous mutants are both resistant to spectinomycin. However, only transplastomic clones are also resistant to streptomycin. Thus, the spectinomycin resistant clones were tested for streptomycin resistance on a C2 medium containing 200 mg $L^{-1}$ streptomycin and 200 mg $L^{-1}$ spectinomycin (FIG. 9B). Out of the 110 spectinomycin resistant clones two were identified as transplastomic by cross-resistance to streptomycin. The transplastomic clones were designated Lf-pZS391B-1 and Lf-pZS391B-2.

Figure 10A:
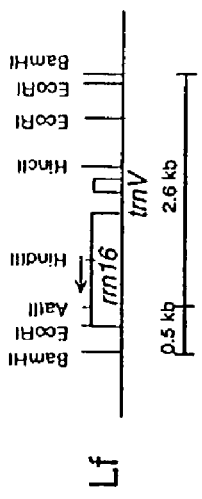
FIG. 10A, Map of the region containing the AatII site. Spectinomycin resistance mutation eliminates the AatII site.
Figure 10B:
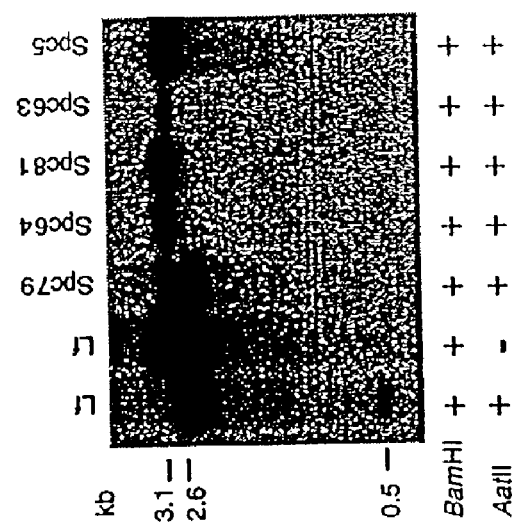
FIG. 10B, BamHI-AatII digested DNA was probed with the EcoRI-HincII fragment (P3 probe, FIG. 8A).

Results of Southern analysis shown in FIG. 10B suggest a uniform population of transformed plastid genome copies (homoplastomic state) in plants Lf-pZS391B-1 and Lf-pZS391B-2. Plants regenerated from the Lf-pZS391B-1 clone were homoplastomic without further purification. Plants regenerated from the Lf-pZS391B-2 clone initially contained a mixed population of wild type and transformed plastid genome copies. Homoplastomic state in this clone was achieved after two cycles of plant regeneration from leaves on a selective spectinomycin medium. Results shown below were obtained with subclone Lf-pZS391B-2NC.

DNA gel blot analysis was used to test for integration of aadA16gfp and flanking pZS391B plastid targeting sequences into the *Lesquerella fendleri* plastid genome. In the left and right targeting regions, HindIII, StuI and EcoRI sites distinguish between the *Lesquerella* genomic sequence and sequences present in vector pZS391B respectively (FIG. 8B). Integration of aadA16gfp was confirmed by probing EcoRI digested DNA with the aadA probe (P1), which hybridizes to a 3.7-kb fragment (FIG. 8C). The segment of plastid genome corresponding to the pZS391B left targeting region in both transgenic lines represent sequences from *Lesquerella* indicating that aadA16gfp integrated by recombination via sequences directly upstream of the marker gene. This conclusion was drawn from probing EcoRI/HindIII/StuI/HincII digested DNA with the tobacco EcoRI-HincII left targeting region (Probe P3) shown in FIG. 8C.

The transplastomic clones differ with respect to the plastid genome segment corresponding to the right targeting region. Clone Lf-pZS391B-1D carries the *Lesquerella* sequence as indicated by the presence of the polymorphic EcoRI site. Thus, in this transplastomic clone, the *Arabidopsis* right targeting region apparently was not incorporated into the *Lesquerella* plastid genome from vector pZS391B. The second clone, Lf-pZS391B-2NC, lacks the polymorphic Lesquerella EcoRI site. Thus, integration in this clone took place close to the end of the vector right targeting sequence replacing the Lesquerella plastid DNA sequence with the Arabidopsis plastid DNA sequence carried by the transformation vector. These conclusions are based on data obtained from probing EcoRI-digested DNA with the HindIII-EcoRI fragment (Probe P2) shown in FIG. 8C.

Figure 9C:
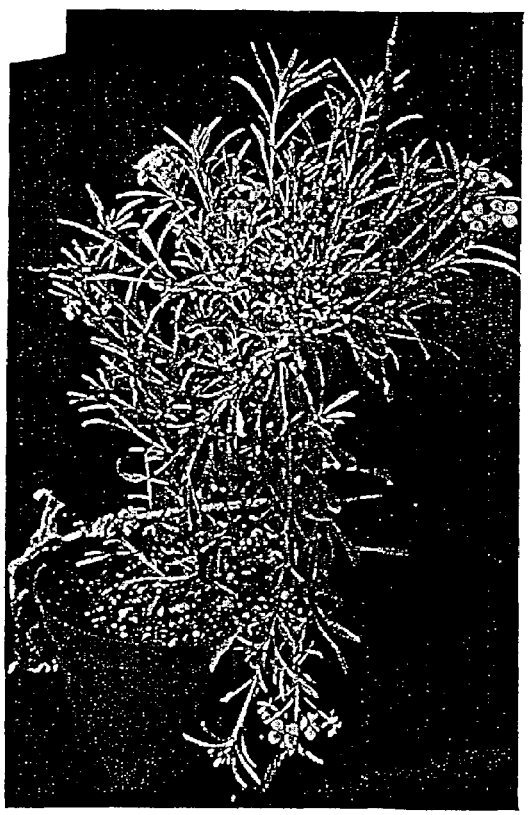
FIG. 9C, Grafted transplastomic plant in greenhouse.
Figure 9D:
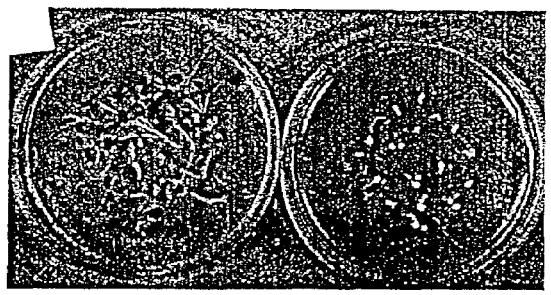
FIG. 9D, Testing resistance in seed progeny from cross Lf-pZS391-1D (maternal parent) and Lf-Spc5 (pollen parent; on left). Wild-type sensitive seedlings are shown on the right. Seeds have been germinated on 100 mg $L^{-1}$ spectinomycin.

Regenerated Lf-pZS391B-1 (subclones D and DD) and wild-type Lesquerella shoots rooted in sterile culture, but did not survive transfer to soil. However, shoots could be grafted onto Brassica napus rootstock, which then flowered and set seed (FIG. 9C). Study of seed transmission of transplastomes was complicated by the lack of wild-type plants with compatible pollen in the greenhouse. However, reciprocal crosses could be made between the transplastomic Lf-pZS391B-1D plant and a spontaneous chloroplast spectinomycin resistant mutant Lf-Spc5 (see below). Both, Lf-pZS391B-1D and Lf-Spc5 plants are resistant to spectinomycin. Chloroplasts of the two lines could be distinguished however, on streptomycin medium: the transplastomic Lf-pZS391B-1D chloroplasts were resistant whereas mutant Lf-Spc5 chloroplasts were sensitive. Seed progeny from a cross using the transplastomic line as female parent segregated for streptomycin resistance (12 greens, 4 whites; 100 mg $L^{-1}$) indicating that the germline is still heteroplastomic (FIG. 9D). Interestingly, Southern analysis of leaf DNA of the same plants did not reveal heteroplastomy (see above). Seed progeny from the cross with the transplastomic clone as pollen parent yielded only streptomycin sensitive progeny (13 whites). Maternal transmission of streptomycin resistance supports chloroplast localization of the aadA16gfp transgene. Further evidence for chloroplast localization of the transgene was obtained by confocal laser microscopy, which shows GFP encoded by the aadA16gfp gene exclusively in chloroplasts (data not shown).

Plants were also regenerated from the second transplastomic clone, Lf-pZS391B-2N. Three of the subclones that were purified to homoplasmy (NC, NE, NF) grew slowly and had abnormal, bushy morphology. No attempt was made to obtain seed from these plants.

Spontaneous Spectinomycin Resistance Mutants

In the bombarded leaf cultures many spectinomycin resistant clones were obtained which did not carry the aadA16gfp gene. This was not surprising, since spontaneous spectinomycin resistant mutants have been reported in a number of species (Fromm et al. 1987; Svab and Maliga 1991; Kavanagh et al. 1994; Sikdar et al. 1998; Sidorov et al. 1999). Spectinomycin resistance may be due to mutations in the plastid rrn16 gene encoding the 16S rRNA. Mutations conferring spectinomycin resistance often eliminate an AatII recognition sequence localized to a conserved stem structure (Fromm et al. 1987; Svab and Maliga 1991).

DNA was isolated from the leaves of five independent spontaneous spectinomycin resistance mutants (Lf-Spc5, -63, -64, -79, -81) to test for the presence of the conserved AatII site. Digestion with BamHI releases a 3.1-kb rrn16 fragment containing the AatII site. Digestion with both BamHI and AatII yields two fragments if the AatII site is present, which are 0.5-kb and 2.6-kb in size (FIG. 10A). Lack of the AatII site in BamHI/AatII digested DNA of four clones, Lf-Spc5, -63, -64 and 81, is indicated by the presence of the larger 3.1-kb fragment (FIG. 10B). One of the clones, Lf-Scp79 probably contains a mixed population of wild-type and mutant plastid genomes since it has all three fragments.

Seed progeny was obtained from one of the spectinomycin resistant mutants, Lf-Spc5. The selfed seed progeny segregated for spectinomycin resistance when germinated on C1 medium containing spectinomycin (100 mg $L^{-1}$). Segregation for resistance in the seed progeny indicates that a mixed population of wild-type and mutant plastid genome has been maintained in the germline.

Discussion

Selection of transplastomic clones in tobacco is carried out in a tissue culture system, in which every cell is able to divide and regenerate shoots (Svab et al. 1990; Svab and Maliga 1993). The selective drug suppresses greening and shoot regeneration; thus the transplastomic clones can be readily recognized by formation of green shoots. Identification of transplastomic clones as callus is also feasible but more difficult since, under the conditions employed, sensitive cells also proliferate at a slow rate and the transplastomic cells may be buried in wild-type tissue. In contrast to tobacco, most Arabidopsis leaf cells don't divide on a shoot regeneration medium. Transplastomic clones can not be recovered from these cells, even if their chloroplast genome has been transformed. Transformation protocols in Arabidopsis as described in Examples I-III, employ a two-stage process to circumvent the problem: the first stage involves induction of cell division (callus formation) from every cell, followed by induction of shoots on a selective medium. The efficiency of plastid transformation in this system is low, yielding only one transplastomic clone per 100 bombarded leaf samples (Sikdar et al. 1998). In tobacco, on average, one bombardment yields a transplastomic event. The tissue culture response of Lesquerella leaf cells is similar to that of tobacco leaf cells; in culture virtually every cell is capable of plant regeneration. However, based on the data presented herein, it appears that plastid transformation efficiency in Lesquerella fendleri is comparable to Arabidopsis, yielding one transplastomic clone in 25 samples. Thus, competence for plastid transformation in Lesquerella is not linked to high regeneration capacity.

High frequency of spontaneous spectinomycin resistant (rrn16) mutants indicates that the Lesquerella tissue culture protocol is eminently suitable for the recovery of transplastomic clones by selection for spectinomycin resistance. What could then be the reason for the low efficiency of plastid transformation? Earlier we speculated, that the relatively short targeting sequence may have been the reason for the inefficiency of plastid transformation in Arabidopsis (Sikdar et al. 1998). In the present study, the plastid targeting region of the vector has been enlarged, and now it is comparable to the size of the tobacco vectors (Zoubenko et al. 1994). Thus, the size of the targeting region does not appear to be the reason for the low transformation efficiency in Arabidopsis. Alternative explanation would be relative inefficiency of the recombination system in both Lesquerella and Arabidopsis.

Southern blot analysis of transplastomic line Lf-pZS391B-1D suggested uniformly transformed plastid genomes in the leaves. However, segregation for antibiotic resistance in the seed progeny indicated a heteroplastomic state in the germline. The types of blots shown in FIG. 8C in tobacco would identify plants, which do not segregate wild-type genome copies in the seed progeny (Carrer et al. 1993; Svab and Maliga 1993). Mutant plastids of the Lf-Spc5 clone also appear to be homoplastomic based on Southern probing for the AatII site (FIG. 10B). Still, the seed progeny segregates for spectinomycin resistance. It is likely that homoplastomic plants can be readily obtained in the second seed progeny, as observed in *Arabidopsis* plastid spectinomycin resistant mutants (data not shown).

Comparative analysis of plastid genomes indicates that while the coding regions are highly conserved, there is a high level of variation in the intergenic regions (Shimada and Sugiura 1991). Is it necessary to construct a plastid vector with homologous targeting sequences for every species? The answer is: probably not, as long as the species are closely related. Potato plastids have been successfully transformed with tobacco plastid targeting sequences (Sidorov et al. 1999) and tobacco plastids have been transformed with *Solanum nigrum* plastid targeting sequences (Kavanagh et al. 1999). It appears, that efficient plastid transformation with heterologous DNA in higher plants is feasible due to diminished mismatch recombination/repair system mediating integration of foreign DNA via multiple recombination events (Kavanagh et al. 1999). Thus, the practical limit to transformation by heterologous vectors is the lack of ability of the recipient's transcription and translation machinery to properly interpret the heterologous gene expression signals. It is interesting in this regard that the transplastomic clones Lf-pZS391B-1D and Lf-pZS391BD2NC differ with respect to vector sequences replacing the cognate recipient genome segments. Lf-pZS391B-1D does not have any of the RFLPs derived from the vector targeting sequence. In contrast, Lf-pZS391BD2NC plastid DNA carries the *Arabidopsis* right targeting region RFLP, which lacks the EcoRI site. Therefore, part of the *Lesquerella* sequence in this transgenic clone has been replaced with the vector right targeting region.

REFERENCES

1. Bendich, A. J. (1987) Why do chloroplasts and mitochondria contain so many copies of their genome? Bioessays 6, 279-282.
2. Bock, R. and Maliga, P. (1995) In vivo testing of a tobacco plastid DNA segment for guide RNA function in psbL editing. Molec. Gen. Genet. 247, 439-443.
3. Carrer, H., Hockenberry, T N, Svab, Z., Maliga, P. (1993) Kanamycin resistance as a selectable marker for plastid transformation in tobacco. Molec. Gen. Genet. 241, 49-56.
4. Carrer, H., Maliga, P. (1995) Targeted insertion of foreign genes into the tobacco plastid genome without physical linkage to the selectable marker gene. Biotechnology 13, 791-794.
5. Czako, M., Wilson, J. and Marton. L. (1993) Sustained root culture for generation and vegetative propagation of transgenic *Arabidopsis thaliana*. Plant Cell Rep. 12, 603-606.
6. Fromm, H., Edelman, M., Aviv, D. and Galun, E. (1987) The molecular basis of basis of rDNA-dependent specinomycin resistance in *Nicotiana* chloroplasts. EMBO J., 6, 3233-3237.
7. Galbright, D. W., Harkins, K. R. and Knapp, S. (1991) Systemic endopolyploidy in *Arabidopsis thallana*. Plant Physiol. 96, 985-989.
8. Golds, T., Maliga, P. & Koop, H. U. (1993) Stable plastid transformation in PEG-teated protoplasts of *Nicotiana tabacum*. Bio/Technology, 11, 95-97
9. Hajdukiewicz, P., Svab, Z. and Maliga, P. (1994) The small, versatile pPZP family of *Agrobacterium* binary vectors for plant transformation. Plant. Mol. Biol. 25, 989-994.
10. Kavanagh T A, O'Driscoll K M, McCabe P F, Dix P J (1994) Mutations conferring lincomycin, spectinomycin, and streptomycin resistance in *Solanum nigrum* are located in three diferent chloroplast genes. Mol Gen Genet 242: 675-680.
11. Kavanagh T A, Thanh N D, Lao N T, McGrath N, Peter S O, Horvath E M, Dix P J, Medgyesy P (1999) Homologous plastid DNA transformation in tobacco is mediated by multiple recombination events. Genetics 152: 1111-1122.
12. Khan M S, Maliga P (1999) Fluorescent antibiotic resistance marker to track plastid transformation in higher plants. Nat Biotechnol 17: 910-915
13. Koop H U, Steinmuler K, Wagner H, Ršssler C, Eibl C, Sacher L (1996) Integration of foreign sequences into the tobacco plastome via PEG-mediated protoplast tranformation. Planta 199: 193-201.
14. Kuroda H, Maliga P (2000) Sequences downstream of the translation initiation codon are important determinants of translation efficiency in chloroplasts. in review:
15. Maliga, P. (1993) Towards plastid transformation in flowering plants. Trends Biotechnol., 11, 101-106.
16. Maliga, P. (1995) Biolistic transformation of tobacco cells with nuclear drug resistance genes. In Methods in Plant Molecular Biology—A Laboratory Manual, (Maliga, P., Klessig, D., Cashmore, A., Gruissem W. and Varner, J., eds.). Cold Spring Harbor: Cold Spring Harbor Laboratory Press, pp. 37-54.
17. Maliga, P., Carrer, H., Kanevski, I., Staub, J., Svab Z. (1993) Plastid engineering in land plants: a conservative genome is open to change. Phil. Trans. R. Soc. Lond. B 341, 449-454.
18. Marton, L. and Browse, 4-7. (1991) Facile transformation of *A-rabidopsis thaliana*. Plant Cell Rep. 10, 235-239.
19. McBride, K. E., Svab, Z., Schaaf, D. J., Hogan, P. S., Stalker, D. M., Maliga, P. (1995) Amplification of a chimeric *Bacillus* gene in chloroplasts leads to an extraordinary level of an insecticidal protein in tobacco. Biotechnology, 13, 362-365.
20. Melaragno, J. E., Mehrotra, B. and Coleman, A. W. (1993) Relationship between endopolyploidy and cell size in epidermal tissue of *Arabidopsis*. Plant Cell 5, 1661 1668.
21. Mettler, I. J. (1987) A simple and rapid method for minipreparation of DNA from tissue cultured plant cells. Plant Mol. Biol. Reporter 5, 346-349.
22. Meyerowitz, E. M. and Somerville, C. R. (1994) *A. rabidopsis*. Cold Spring Harbor: Cold Spring Harbor Laboratory Press.
23. Murashige, T. and Skoog, F. (1962) A revised medium for rapid growth and bioassays with tobacco tissue culture. Physiol. Plant., 15, 493-497.
24. O'Neill, C, Horvath, G. V., Horvath, E., Dix, P. J. and Medgyesy, P. (1993) Chloroplast transformation in plants: polyethylene glycol (PEG) treatment of protoplasts is an alternative to biolistic delivery systems. Plant J., 3, 729-738.
25. Palmer, J. D. (1991) Plastid chromosomes: structure and evolution. In The Molecular Biology of Plastids, Cell Culture and Somatic Cell Genetics of Plants, vol. 7A (L. Bogorad, L. and Vasil I. K. eds.). San Diego: Academic Pressf pp. 5-53.
26. Palmer, J. D., Downie, S. R., Nugent, J. M., Brandt, P., Unseld, M., Klein, M., Brennicke, A., Schuster, W. and Borner, T. (1994) Chloroplast and mitochondrial DNAs of *Arabidopsis thaliana*: conventional genomes in an unconventional plant. In *Arabidopsis*, (Meyerowitz, E. M. and Somerville, C. R.,*eds.) Cold Spring Harbor: Cold Spring Harbor Laboratory Press, pp. 37-62.
27. Shimada H, Sugiura M (1991) Fine structural features of the chloroplast genome: comparison of the sequenced chloroplast genomes. Nucleic Acids Res 19: 983-995
28. Shinozaki, K., Ohme, M., Tanaka, M., Wakasugi, T., Hayashida, N., Matsubayashi, T., Zaita, N., Chunwongse, J., Obokata, J., Yamaguchi-Shinozaki, K., Ohto, C., Torazawa, K., Meng, B. Y., Sugita, M., Deno, H., Kamoyashira, T., Yamada, K., Kusuda, J., Takawa, F., Kato, A., Tohdoh, N., Shimada, H. and Suguira, M. (1986) The complete nucleotide sequence of the tobacco chloroplast genome: its gene organization and expression. EMBO J., 5, 2043-2049.
29. Sidorov V A, Kasten D, Pang S Z, Hajdukiewicz P T J, Staub J M, Nehra N S (1999) Stable chloroplast transformation in potato: use of green fluorescent protein as a plastid marker. Plant J 19: 209-216.
30. Sikdar S R, Serino G, Chaudhuri S, Maliga P (1998) Plastid transformation in *Arabidopsis thaliana*. Plant Cell Rep 18: 20-24.
31. Skarzhinskaya M, Landgren M, Glimelius K (1996) Production of intertribal somatic hybrids between *Brassica napus* and *Lesquerella fendleri* (Gray) Wats. Theor Appl Genet 93: 1242-1250.
32. Staub, J. & Maliga, P. (1992) Long regions of homologous DNA are incorporated into the tobacco plastid genome by transformation. Plant Cell 4, 39-45.
33. Svab, Z. and Maliga, P. (1991) Mutation proximal to the tRNA binding region of the *Nicotiana* plastid 16S rRNA confers resistance to spectinomycin. Molec. Gen. Genet. 228, 316-319.
34. Svab, Z. and Maliga, P. (1993) High-frequency plastid transformation in tobacco by selection for a chimeric aadA gene. Proc. Natl. Acad. Sci. USA, 90, 913 917.
35. Svab, Z. and Maliga, P. (1993) High-frequency plastid transformation in tobacco by selection for a chimeric aadA gene. Proc. Natl. Acad. Sci. USA, 90, 913 917.
36. Svab, Z., Hajdukiewicz, P. and Maliga, P. (1990a) Stable transformation of plastids in higher plants. Proc. Natl. Acad. Sci. USA, 87, 8526-8530
37. Svab, Z., Harper, E. C., Jones, J. D. G. and Maliga, P. (1990b) Aminoglycoside-3"-adenyltransferase confers resistance to spectinomycin and streptomycin in *Nicotiana tabacum*. Plant Mol. Biol. 14, 197-205.
38. Valvekens, D., Van Motagu, M. and Van Lijsebettens, M. (1988) *Agrobacterium tumefaciens* mediated transformation of *Arabidopsis thaliana* root explants using kanamycin selection. Proc. Natl. Acad. Sci. USA 85, 5536-5540.
39. Zoubenko, O. V., Allison, L. A., Svab, Z. and Maliga, P. (1994) Efficient targeting of foreign genes into the tobacco plastid genome. Nucleic Acids Res., 22, 3819-3824.
40. Feldmann, K. A. and Marks, M. D. (1986) Rapid and efficient regeneration of plants from explants of *Arabidopsis thaliana*. Plant Sci. 47: 63-69.
41. Lloyd, A. M., Barnason, A. R., Rogers, S. G., Byrne, M. C., Fraley, R. T., Horsch, R. B. (1986) Science 234:464-466.
42. Patton, D. A. and Meinke, D. W. (1988) High-frequency plant regeneration from cultured cotyledons of *Arabidopsis thaliana*. Plant Cell Reports 7:233-237.
43. Van der Graaff, E. and Hooykaas, P. J. J. (1996) Improvements in the transformation of *Arabidopsis thaliana* C24 leaf-discs by *Agrobacterium tumefaciens* Plant Cell Rep. 15: 572-577.
44. Pelletier, G., Primard, C., Vedel, F., Chetrit, P. Remy, R. Rousselle, R. and Renard M. (1983) Intergeneric cytoplasmic hybridization in cruciferae by protoplast fusion. Mol. Gen. Genet. 191:244-250.
45. Radke, S. E., Turner, J. C., and Facciotti D. (1992) Transformation and regereation of *Brassica rapa* using *Agrobacterium tumefaciens*. Plant Cell Reports 11:499-505.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. An improved vector for transforming plastids of higher plants, said vector comprising a targeting segment having first and second targeting sequences for facilitating recombination within the plastid genome within 16S rRNA encoding sequences, each of said first and second targeting sequences flanking at least one transgene of interest, wherein one of said first and second targeting sequence is chimeric, said chimeric targeting sequence having a first portion of a 16S rRNA gene from the plant species targeted for transformation, and a second portion of a 16S rRNA gene from a different plant species.

2. A vector as claimed in claim 1, wherein said first targeting sequence is chimeric and is obtained from *Brassica* and *Tobacco*.

3. A vector as claimed in claim 1, wherein said second targeting sequence is chimeric and is obtained from *Brassica* and *Tobacco*.

4. A vector as claimed in claim 1, wherein said at least one transgene is a selectable marker gene.

5. A vector as claimed in claim 1, wherein said at least one transgene is a herbicide resistance gene.

6. A vector as claimed in claim 1, wherein said at least one transgene is a drought resistance gene.

7. A vector as claimed in claim 1, said vector comprising the plastid targeting sequence of SEQ ID NO: 4.

8. A transgenic plant comprising the vector of claim 1.

9. A transgenic plant comprising the vector of claim 7.

10. A transgenic *Brassica* ssp. plant comprising the vector of claim 1.

11. A transformed plant cell comprising the vector of claim 1.

12. A transformed plant cell as claimed in claim 11, said cell being selected from the group consisting of cotyledon cells, leaf cells, hypocotyls and root cells.

13. A vector as claimed in claim 1, wherein said at least one transgene constitutes a monocistronic expression unit.

14. A vector as claimed in claim 1, wherein said at least one transgene constitutes a polycistronic expression unit comprising a selectable marker gene and a foreign gene of interest, wherein said chimeric targeting sequence is obtained from 16S rRNA encoding sequences from *Tobacco* and *Brassica*.

15. A vector as claimed claim 4, wherein said selectable marker gene encodes a peptide conferring resistance to a selection agent which is selected from the group consisting of kanamycin, streptomycin, and spectinomycin.

16. A transgenic *Brassica* plant transformed with the vector of claim 14.

17. A vector as claimed in claim 1, wherein said plastids are chloroplasts.

18. An improved vector for transforming plastids of *Brassica* ssp. and *Nicotiana* and generation of transplastomic plants therefrom, said vector comprising a targeting segment having first and second targeting sequences for facilitating homologous recombination into 16S rRNA encoding sequences within the plastid genome, each of said first and second targeting sequences flanking at least one transgene of interest, wherein one of said first and second targeting sequences is chimeric, said chimeric targeting sequence being obtained from the 16S rRNA genes of *Tobacco* and *Brassica*.

19. A vector as claimed in claim 18, wherein said first targeting sequence is chimeric.

20. A vector as claimed in claim 18, wherein said second targeting sequence is chimeric.

21. A vector as claimed in claim 18, wherein said at least one transgene is a selectable marker gene.

22. A vector as claimed in claim 18, wherein said at least one transgene is a herbicide resistance gene.

23. A vector as claimed in claim 18, wherein said at least one trans gene is a drought resistance gene.

24. A vector for transforming plastids of *Brassica* ssp. and *Nicotiana* and generation of transplastomic plants therefrom, said vector comprising a targeting segment having first and second targeting sequences for facilitating homologous recombination within the plastid genome, each of said first and second targeting sequences flanking at least one transgene of interest, wherein one of said first and second targeting sequences being chimeric, said chimeric targeting sequence having a first portion derived from the plant species targeted for transformation, and a second portion derived from a different plant species, said chimeric targeting sequence comprising SEQ ID NO: 4.

25. A transgenic plant comprising the vector of claim 18.

26. A transgenic plant comprising the vector of claim 24.

27. A transgenic *Brassica* ssp. plant comprising the vector of claim 18.

28. A transformed plant cell comprising the vector of claim 18.

29. A transformed plant cell as claimed in claim 28, said cell being selected from the group consisting of cotyledon cells, leaf cells, hypocotyls and root cells.

30. A vector as claimed in claim 18, wherein said at least one transgene constitutes a monocistronic expression unit.

31. A vector as claimed in claim 18, wherein said at least one transgene constitutes a polycistronic expression unit comprising a selectable marker gene and a foreign gene of interest.

32. A vector as claimed in claim 21, wherein said selectable marker gene encodes a peptide conferring resistance to a selection agent which is selected from the group consisting of kanamycin, streptomycin, and spectinomycin.

33. A transgenic *Brassica* plant transformed with the vector of claim 24.

34. A vector as claimed in claim 18, wherein said plastids are chloroplasts.

* * * * *